(12) United States Patent
Hourmand et al.

(10) Patent No.: US 11,511,043 B2
(45) Date of Patent: Nov. 29, 2022

(54) SYRINGE CARRIER

(71) Applicant: Sanofi-Aventis Deutschland GMBH, Frankfurt am Main (DE)

(72) Inventors: Yannick Hourmand, Cambridge (GB); Douglas Ivan Jennings, Hertfordshire (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 48 days.

(21) Appl. No.: 17/381,737

(22) Filed: Jul. 21, 2021

(65) Prior Publication Data

US 2021/0346604 A1 Nov. 11, 2021

Related U.S. Application Data

(63) Continuation of application No. 17/020,027, filed on Sep. 14, 2020, which is a continuation of application (Continued)

(30) Foreign Application Priority Data

Dec. 8, 2011 (EP) .................... 11192585

(51) Int. Cl.
*A61M 5/31* (2006.01)
*A61M 5/24* (2006.01)
*A61M 5/32* (2006.01)

(52) U.S. Cl.
CPC ............... *A61M 5/31* (2013.01); *A61M 5/24* (2013.01); *A61M 5/321* (2013.01); *A61M 5/3202* (2013.01); *A61M 2005/2407* (2013.01); *A61M 2005/2414* (2013.01); *A61M 2005/2437* (2013.01)

(58) Field of Classification Search
CPC ........ A61M 2005/206; A61M 2207/00; A61M 2209/00; A61M 5/20; A61M 5/2033; A61M 5/24; A61M 5/31; A61M 2005/2407; A61M 2005/244
See application file for complete search history.

(56) References Cited

U.S. PATENT DOCUMENTS

| | | | |
|---|---|---|---|
| 3,026,873 A | 3/1962 | Miskel et al. | |
| 3,076,455 A | 2/1963 | McConnaughey et al. | |
| 3,144,178 A | 8/1964 | Sarnoff | |
| 3,880,163 A | 4/1975 | Ritterskamp | |

(Continued)

FOREIGN PATENT DOCUMENTS

| | | |
|---|---|---|
| CA | 2212489 | 2/1998 |
| CN | 101022841 | 5/2005 |

(Continued)

OTHER PUBLICATIONS

EP Observations by a Third Party in Patent Appln. No. 16195290.8, dated Aug. 24, 2021, 5 pages.

(Continued)

*Primary Examiner* — William R Carpenter
(74) *Attorney, Agent, or Firm* — Fish & Richardson P.C.

(57) ABSTRACT

Described is a syringe carrier comprising a body adapted to receive a barrel of a syringe. The body includes two sections having distal ends with shoulder sections. The shoulder sections are adapted to engage a circumferential gap between the barrel of the syringe and a needle shield covering a needle of the syringe.

15 Claims, 10 Drawing Sheets

Related U.S. Application Data

No. 16/353,282, filed on Mar. 14, 2019, which is a continuation of application No. 15/976,824, filed on May 10, 2018, now Pat. No. 10,646,656, which is a continuation of application No. 14/362,537, filed as application No. PCT/EP2012/074466 on Dec. 5, 2012, now Pat. No. 10,434,258.

(56) References Cited

U.S. PATENT DOCUMENTS

| | | |
|---|---|---|
| 4,563,175 A | 1/1986 | Lafond |
| 4,643,724 A | 2/1987 | Jobe |
| 4,655,751 A | 4/1987 | Harbaugh |
| 4,735,311 A | 4/1988 | Lowe et al. |
| 4,838,857 A | 6/1989 | Strowe et al. |
| 4,871,355 A | 10/1989 | Kikkawa |
| 4,909,791 A | 3/1990 | Norelli |
| 4,931,040 A | 6/1990 | Haber et al. |
| 4,946,447 A | 8/1990 | Hardcastle et al. |
| 4,964,866 A | 10/1990 | Szwarc |
| 4,973,318 A | 11/1990 | Holm et al. |
| 4,990,142 A | 2/1991 | Hoffman et al. |
| 4,997,422 A * | 3/1991 | Chow ............... A61M 5/3243 604/198 |
| 5,000,744 A | 3/1991 | Hoffman et al. |
| 5,078,698 A | 1/1992 | Stiehl et al. |
| 5,085,641 A | 2/1992 | Sarnoff et al. |
| 5,163,918 A | 11/1992 | Righi et al. |
| 5,169,392 A | 12/1992 | Ranford et al. |
| 5,282,793 A | 2/1994 | Larson |
| 5,320,609 A | 6/1994 | Haber et al. |
| 5,322,511 A | 6/1994 | Armbruster et al. |
| 5,344,407 A | 9/1994 | Ryan |
| 5,350,367 A | 9/1994 | Stiehl et al. |
| 5,356,395 A | 10/1994 | Chen |
| 5,368,578 A | 11/1994 | Covington et al. |
| 5,383,858 A | 1/1995 | Reilly et al. |
| 5,383,863 A | 1/1995 | Mardones |
| 5,439,450 A | 8/1995 | Haedt |
| 5,451,214 A | 9/1995 | Hajishoreh |
| 5,480,387 A | 1/1996 | Gabriel et al. |
| 5,520,653 A | 5/1996 | Reilly et al. |
| 5,599,309 A | 2/1997 | Marshall et al. |
| 5,637,101 A | 6/1997 | Shillington |
| 5,709,662 A | 1/1998 | Olive et al. |
| 5,779,675 A | 7/1998 | Uber et al. |
| 5,865,805 A | 2/1999 | Ziemba |
| 5,913,844 A | 6/1999 | Fago et al. |
| 5,925,032 A * | 7/1999 | Clements ............... A61M 5/34 606/1 |
| 5,928,205 A | 7/1999 | Marshall |
| 5,928,698 A | 7/1999 | Soyad |
| 6,059,756 A | 5/2000 | Yeh |
| 6,090,082 A | 7/2000 | King et al. |
| 6,203,530 B1 | 3/2001 | Stewart |
| 6,210,369 B1 | 4/2001 | Wilmot et al. |
| 6,371,939 B2 | 4/2002 | Bergens et al. |
| 6,454,743 B1 | 9/2002 | Weber |
| 6,544,234 B1 | 4/2003 | Gabriel |
| 6,613,022 B1 | 9/2003 | Doyle |
| 6,656,163 B1 | 12/2003 | Marshall et al. |
| 6,726,657 B1 | 4/2004 | Dedig et al. |
| 6,743,205 B2 | 6/2004 | Nolan, Jr. et al. |
| 7,118,552 B2 | 10/2006 | Shaw et al. |
| 7,288,078 B2 | 10/2007 | Fitzgerald |
| 7,717,877 B2 | 5/2010 | Lavi et al. |
| 8,647,299 B2 | 2/2014 | Stamp |
| 8,845,594 B2 | 9/2014 | Jennings |
| 8,876,785 B2 | 11/2014 | Holmqvist |
| 8,900,197 B2 | 12/2014 | Crow |
| 8,992,746 B2 | 3/2015 | Miyaji et al. |
| 9,072,833 B2 | 7/2015 | Jennings et al. |
| 9,216,256 B2 | 12/2015 | Olson et al. |
| 9,233,213 B2 | 1/2016 | Olson et al. |
| 9,242,053 B2 | 1/2016 | Wozencroft |
| 9,289,554 B2 | 3/2016 | Hourmand et al. |
| 9,408,970 B2 | 8/2016 | Hourmand et al. |
| 9,713,678 B2 | 7/2017 | Hourmand et al. |
| 9,757,520 B2 | 9/2017 | Corrigan |
| 9,867,940 B2 | 1/2018 | Holmqvist et al. |
| 10,918,803 B2 | 2/2021 | Kemp et al. |
| 11,103,649 B2 | 8/2021 | Kemp et al. |
| 2001/0011163 A1 | 8/2001 | Nolan, Jr. et al. |
| 2002/0083564 A1 | 7/2002 | James |
| 2003/0105430 A1 | 6/2003 | Lavi et al. |
| 2004/0039336 A1 | 2/2004 | Amark et al. |
| 2004/0108339 A1 | 6/2004 | Hansen et al. |
| 2005/0020979 A1 | 1/2005 | Westbye et al. |
| 2005/0027255 A1 | 2/2005 | Lavi et al. |
| 2005/0075608 A1 | 4/2005 | Holdgate et al. |
| 2005/0101919 A1 | 5/2005 | Brunnberg |
| 2005/0115507 A1 | 6/2005 | Halachmi et al. |
| 2005/0165353 A1 * | 7/2005 | Pessin ............... A61M 5/3272 604/110 |
| 2005/0277896 A1 | 12/2005 | Messerli et al. |
| 2006/0036216 A1 | 2/2006 | Rimlinger et al. |
| 2006/0161114 A1 | 7/2006 | Perot et al. |
| 2006/0167412 A1 | 7/2006 | Marshall |
| 2006/0184133 A1 * | 8/2006 | Pessin ............... A61M 5/3257 604/198 |
| 2007/0173770 A1 | 7/2007 | Stamp |
| 2007/0260348 A1 | 11/2007 | Gordils |
| 2008/0147003 A1 | 6/2008 | Menzi et al. |
| 2008/0228143 A1 | 9/2008 | Stamp |
| 2008/0262427 A1 | 10/2008 | Hommann |
| 2009/0012471 A1 * | 1/2009 | Harrison ............... A61M 5/2033 604/136 |
| 2009/0105663 A1 | 4/2009 | Brand et al. |
| 2009/0254027 A1 | 10/2009 | Moeller |
| 2010/0152655 A1 * | 6/2010 | Stamp ............... A61M 5/2033 604/110 |
| 2010/0179507 A1 | 7/2010 | Hess et al. |
| 2010/0185178 A1 | 7/2010 | Sharp et al. |
| 2012/0053528 A1 | 3/2012 | Bollenbach et al. |
| 2012/0130321 A1 | 5/2012 | Woehr |
| 2012/0186075 A1 | 7/2012 | Edginton |
| 2013/0220869 A1 | 8/2013 | Klintenstedt et al. |
| 2014/0243753 A1 | 8/2014 | Bostrom |
| 2014/0249479 A1 | 9/2014 | Pfrang |
| 2014/0323985 A1 | 10/2014 | Hourmand et al. |
| 2014/0330213 A1 | 11/2014 | Hourmand et al. |
| 2014/0336590 A1 | 11/2014 | Hourmand et al. |
| 2018/0140781 A1 | 5/2018 | Kemp et al. |
| 2018/0140782 A1 | 5/2018 | Kemp et al. |
| 2020/0405961 A1 * | 12/2020 | Hourmand ............... A61M 5/31 |
| 2021/0077743 A1 | 3/2021 | Kemp et al. |
| 2022/0016358 A1 | 1/2022 | Kemp et al. |

FOREIGN PATENT DOCUMENTS

| | | |
|---|---|---|
| CN | 1911467 | 8/2006 |
| CN | 2925504 | 7/2007 |
| CN | 101400393 | 4/2009 |
| CN | 101420995 | 4/2009 |
| CN | 201213944 | 4/2009 |
| CN | 103945879 | 7/2014 |
| DE | 202009009119 | 12/2009 |
| EA | 012008 | 6/2009 |
| EA | 013934 | 8/2010 |
| EP | 0518416 | 12/1992 |
| EP | 0692272 | 1/1996 |
| EP | 1702643 | 9/2006 |
| EP | 2279771 | 2/2011 |
| EP | 2438952 | 4/2012 |
| EP | 2727617 | 6/2012 |
| EP | 2777684 | 9/2014 |
| EP | 2788052 | 9/2015 |
| EP | 3153197 | 4/2017 |
| FR | 2764195 | 12/1998 |
| GB | 407109 | 3/1934 |
| GB | 829724 | 3/1960 |
| GB | 1122592 | 8/1968 |
| GB | 2388033 | 11/2003 |

(56) References Cited

FOREIGN PATENT DOCUMENTS

| | | |
|---|---|---|
| GB | 2396298 | 6/2004 |
| GB | 2397767 | 8/2004 |
| GB | 2447339 | 9/2008 |
| GB | 2434317 | 1/2011 |
| GB | 2471473 | 1/2011 |
| JP | H08-10324 | 1/1996 |
| JP | 2002-503127 | 1/2002 |
| JP | 2005-021247 | 1/2005 |
| JP | 2005-536300 | 12/2005 |
| JP | 2006-507903 | 3/2006 |
| JP | 2006-516901 | 7/2006 |
| JP | 2008-500854 | 1/2008 |
| JP | 2009-077943 | 4/2009 |
| JP | 2009-523587 | 6/2009 |
| JP | 2009-529395 | 8/2009 |
| JP | 2014-500086 | 1/2014 |
| JP | 2014-500089 | 1/2014 |
| RU | 2068708 | 11/1996 |
| RU | 2172638 | 8/2001 |
| RU | 2311203 | 11/2007 |
| RU | 2363500 | 8/2009 |
| RU | 2012137269 | 3/2014 |
| WO | WO 1998/035714 | 8/1998 |
| WO | WO 1998/056442 | 12/1998 |
| WO | WO 1999/010030 | 3/1999 |
| WO | WO 1999/022792 | 5/1999 |
| WO | WO 2000/024441 | 5/2000 |
| WO | WO 2001/008727 | 2/2001 |
| WO | WO 2001/060435 | 8/2001 |
| WO | WO 2001/093926 | 12/2001 |
| WO | WO 2002/047746 | 6/2002 |
| WO | WO 2003/013632 | 2/2003 |
| WO | WO 2003/068297 | 8/2003 |
| WO | WO 2003/099358 | 12/2003 |
| WO | WO 2004/007006 | 1/2004 |
| WO | WO 2004/020026 | 3/2004 |
| WO | WO 2004/050150 | 6/2004 |
| WO | WO 2005/001161 | 1/2005 |
| WO | WO 2013/083614 | 6/2005 |
| WO | WO 2005/070481 | 8/2005 |
| WO | WO 2005/083614 | 9/2005 |
| WO | WO 2005/115506 | 12/2005 |
| WO | WO 2005/115507 | 12/2005 |
| WO | WO 2006/047810 | 5/2006 |
| WO | WO 2006/085176 | 8/2006 |
| WO | WO 2006/106291 | 10/2006 |
| WO | WO 2006/106295 | 10/2006 |
| WO | WO 2007/056792 | 5/2007 |
| WO | WO 2007/083115 | 7/2007 |
| WO | WO 2007/104636 | 9/2007 |
| WO | WO 2007/129106 | 11/2007 |
| WO | WO 2009/019437 | 2/2009 |
| WO | WO 2009/022132 | 2/2009 |
| WO | WO 2010/072644 | 7/2010 |
| WO | WO 2010/097116 | 9/2010 |
| WO | WO 2010/115822 | 10/2010 |
| WO | WO 2010/136078 | 12/2010 |
| WO | WO 2010/147553 | 12/2010 |
| WO | WO 2011/000570 | 1/2011 |
| WO | WO 2011/001161 | 1/2011 |
| WO | WO 2011/101378 | 8/2011 |
| WO | WO 2012/073032 | 6/2012 |
| WO | WO 2012/089445 | 7/2012 |
| WO | WO 2012/164403 | 12/2012 |
| WO | WO 2013/072182 | 5/2013 |

OTHER PUBLICATIONS

Anders Holmqqvist, and Hsueh-Yi Chen, *Junior Party (U.S. Appl. No. 17/020,027)* v. *Yannick Hourmand, Douglas Ivan Jennings, and Matthew Ekman, Senior Party (U.S. Appl. No. 17/020,027)*, Declaration of Interference, Patent Interference No. 106,135, filed Aug. 26, 2021, 8 pages.

CN Search Report in Chinese Appln. 201280069195.4, dated Dec. 5, 2012, 2 pages (with English translation).
CN Search Report in Chinese Appln. 201280069203.5, dated Oct. 9, 2015, 2 pages (with English translation).
EP Extended Search Report in European Appln. 16195290.8, dated Mar. 15, 2017, 6 pages.
EP Extended Search Report in European Appln. 16195292.4, dated Mar. 17, 2015, 6 pages.
EP Search Report in European Appln. 11192585.5, dated Apr. 20, 2012, 5 pages.
Merriamebster.com [online], "Hinge," Retrieved on Dec. 18, 2016, retrieved from URL <https://www.merriamwebster.com/dictionary/hinge>, 14 pages.
PCT International Preliminary Report on Patentability in International Appln No. PCT/EP2016/062462, dated Dec. 5, 2017, 7 pages.
PCT International Preliminary Report on Patentability in International Appln. No. PCT/EP2012/074466, dated Jun. 10, 2014, 5 pages.
PCT International Preliminary Report on Patentability in International Appln. No. PCT/EP2012/074468, dated Jun. 10, 2014, 5 pages.
PCT International Preliminary Report on Patentability in International Appln. No. PCT/EP2012/074469, dated Jun. 10, 2014, 5 pages.
PCT International Preliminary Report on Patentability in International Appln. No. PCT/EP2012/074471, dated Jun. 10, 2014, 6 pages.
PCT International Preliminary Report on Patentability in International Appln. No. PCT/EP2016/062503, dated Dec. 5, 2017, 6 pages.
PCT International Search Report and Written Opinion in International Appln. No. PCT/EP2012/074466, dated Feb. 7, 2013, 9 pages.
PCT International Search Report and Written Opinion in International Appln. No. PCT/EP2012/074468, dated Mar. 13, 2013, 7 pages.
PCT International Search Report and Written Opinion in International Appln. No. PCT/EP2012/074469, dated Feb. 26, 2013, 7 pages.
PCT International Search Report and Written Opinion in International Appln. No. PCT/EP2012/074471, dated Mar. 22, 2013, 8 pages.
PCT International Search Report and Written Opinion in International Appln. No. PCT/EP2016/062462, dated Sep. 27, 2016, 10 pages.
PCT International Search Report and Written Opinion in International Appln. No. PCT/EP2016/062503, dated Aug. 17, 2016, 9 pages.
PCT International Search Report and Written Opinion in International Appln. No. PCT/GB2005/002108, dated Sep. 6, 2005, 2 pages.
PCT International Search Report in International Appln. No. PCT/EP2011/052300, dated Jun. 16, 2011, 4 pages.
PCT International Search Report in International Appln. No. PCT/US00/20623, dated Nov. 21, 2000, 3 pages.
U.S. Appl. No. 14/362,537, filed Jun. 3, 2014, Yannick Hourmand.
U.S. Appl. No. 15/976,824, filed May 10, 2018, Yannick Hourmand.
U.S. Appl. No. 16/353,268, filed Mar. 14, 2019, Yannick Hourmand.
U.S. Appl. No. 16/353,282, filed Mar. 14, 2019, Yannick Hourmand.
U.S. Appl. No. 17/020,027, filed Sep. 14, 2020, Yannick Hourmand.
U.S. Appl. No. 17/019,879, filed Sep. 14, 2020, Yannick Hourmand.
U.S. Appl. No. 14/362,538, filed Jun. 3, 2014, Yannick Hourmand.
U.S. Appl. No. 14/362,539, filed Jun. 3, 2014, Yannick Hourmand.
U.S. Appl. No. 14/363,400, filed Jun. 6, 2014, Yannick Hourmand.
U.S. Appl. No. 15/579,022, filed Dec. 1, 2017, Thomas Mark Kemp.
U.S. Appl. No. 16/950,510, filed Nov. 17, 2020, Thomas Mark Kemp.
U.S. Appl. No. 15/579,024, filed Dec. 1, 2017, Thomas Mark Kemp.
Brief Communication in European Opposition in Application No. 12795446.9, dated Feb. 18, 2022, 34 pages.
Brief Communication in European Opposition in Application No. 12795446.9, dated Jan. 18, 2022, 57 pages.
Notice of Opposition in European Application No. 12795446.9, dated Aug. 19, 2021, 36 pages.

(56) References Cited

OTHER PUBLICATIONS

SHL Medical AG (Inventors: Anders Holmqvist, and Hsueh-Yi Chen) Junior Party (U.S. Appl. No. 17/020,027) v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Exhibit 2010—Merriam-Webster Definition of C-shaped, dated Jan. 10, 2021, 2 pages.
SHL Medical AG (Inventors: Anders Holmqvist, and Hsueh-Yi Chen) Junior Party (U.S. Appl. No. 17/020,027) v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Exhibit 2023—Transcript of Videotaped Deposition of Nigel David Harrison, dated Feb. 18, 2022, 234 pages.
SHL Medical AG (Inventors: Anders Holmqvist, and Hsueh-Yi Chen) Junior Party (U.S. Appl. No. 17/020,027) v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,13 5, Exhibit 2022: Declaration of Neil Sheehan, filed Apr. 6, 2022, 27 pages.
SHL Medical AG (Inventors: Anders Holmqvist, and Hsueh-Yi Chen) Junior Party (U.S. Appl. No. 17/020,027) v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,13 5, Exhibit 1001—Declaration of Nigel David Harrison, dated Dec. 11, 2021, 19 pages.
SHL Medical AG (Inventors: Anders Holmqvist, and Hsueh-Yi Chen) Junior Party (U.S. Appl. No. 17/020,027) v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Exhibit 1013—Declaration of Gordon D. Row, MS, filed Apr. 7, 2022, 30 pages.
SHL Medical AG (Inventors: Anders Holmqvist, and Hsueh-Yi Chen) Junior Party (U.S. Appl. No. 17/020,027) v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Exhibit 1014—Transcript of Remote Deposition of Neil Sheehan taken Mar. 3, 2022, 105 pages.
SHL Medical AG (Inventors: Anders Holmqvist, and Hsueh-Yi Chen) Junior Party (U.S. Appl. No. 17/020,027) v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Exhibit 1015—Claim Chart demonstrating support for Sanofi's independent claim 2, filed Apr. 7, 2022, 11 pages.
SHL Medical AG (Inventors: Anders Holmqvist, and Hsueh-Yi Chen) Junior Party (U.S. Appl. No. 17/020,027) v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, SHL Medical Annotated Copy of Claims, filed Sep. 23, 2021, 9 pages.
SHL Medical AG (Inventors: Anders Holmqvist, and Hsueh-Yi Chen) Junior Party (U.S. Appl. No. 17/020,027) v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, SHL Medical Motion 2 (To Deny Benefit Accorded to Sanofi for Count 1), filed Dec. 15, 2021, 30 pages.
SHL Medical AG (Inventors: Anders Holmqvist, and Hsueh-Yi Chen) Junior Party (U.S. Appl. No. 17/020,027) v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, SHL Medical Motion 1 (For Judgment of No. Written Description for Sanofi's Involved Claims), filed Dec. 15, 2021, 30 pages.
SHL Medical AG (Inventors: Anders Holmqvist, and Hsueh-Yi Chen) Junior Party (U.S. Appl. No. 17/020,027) v. Sanofi-Aventis Deutschland Gmbh (Inventors: Yannick Hourmand, Douglas Ivan Jennings, and Matthew Ekman), Senior Party (U.S. Appl. No. 17/020,027), Patent Interference No. 106,135, SHL Opposition 1, filed Apr. 7, 2022, 34 pages.
SHL Medical AG (Inventors: Anders Holmqvist, and Hsueh-Yi Chen) Junior Party (U.S. Appl. No. 17/020,027), v. Sanofi-Aventis Deutschland GMBH (Inventors: Yannick Hourmand, Douglas Ivan Jennings, and Matthew Ekman Senior Party (U.S. Appl. No. 17/020,027), Patent Interference No. 106,135, Sanofi Opposition 1 (Opposing SHL Motion 1 for Judgment for No Written Description), filed Apr. 7, 2022, 36 pages.
SHL Medical AG (Inventors: Anders Holmqvist, and Hsueh-Yi Chen) Junior Party (U.S. Appl. No. 17/020,027), v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Sanofi-Aventis Motion 1 for Judgment under for Lack of Written Description under Section 112, filed Dec. 15, 2021, 28 pages.
SHL Medical AG (Inventors: Anders Holmqvist, and Hsueh-Yi Chen) Junior Party (U.S. Appl. No. 17/020,027), v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Sanofi-Aventis Annotated Copy of Claims, filed Sep. 23, 2021, 7 pages.
SHL Medical AG (Inventors: Anders Holmqvist, and Hsueh-Yi Chen) Junior Party (U.S. Appl. No. 17/020,027), v. Sanofi-Aventis Deutschland Gmbh (Inventors: Yannick Hourmand, Douglas Ivan Jennings, and Matthew Ekman), Senior Party (U.S. Appl. No. 17/020,027), Patent Interference No. 106,135, Sanofi Opposition 2 (Opposing SHL Motion 2 to Deny Benefit Accorded to Sanofi for Count 1), filed Apr. 7, 2022, 38 pages.
Dictionary.com [online], "Circlip," 2016, retrieved on Feb. 24, 2022, retrieved from URL <https://www.dictionary.com/browse/circlip>, 4 pages.
Brief Communication in European Opposition in Application No. 12795446.9, dated May 16, 2022, 15 pages.
Office Action in U.S. Appl. No. 16/871,897, dated May 18, 2022, 26 pages.
SHL Medical AG (Inventors: Anders Holmqvist, and Hsueh-Yi Chen) Junior Party (U.S. Appl. No. 17/020,027), v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Transcript of Deposition of Gordon Row, dated May 6, 2022, 61 pages.
SHL Medical AG (Inventors: Anders Holmqvist, and Hsueh-Yi Chen) Junior Party (U.S. Appl. No. 17/020,027), v. Sanofi-Aventis Deutschland Gmbh (Inventors: Yannick Hourmand, Douglas Ivan Jennings, and Matthew Ekman), Senior Party (U.S. Appl. No. 17/020,027), Patent Interference No. 106,135, SHL Reply 1, dated May 24, 2022, 34 pages.
SHL Medical AG (Inventors: Anders Holmqvist, and Hsueh-Yi Chen) Junior Party (U.S. Appl. No. 17/020,027), v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, SHL Reply 2, dated May 24, 2022, 35 pages.
SHL Medical AG (Inventors: Anders Holmqvist, and Hsueh-Yi Chen) Junior Party (U.S. Appl. No. 17/020,027), v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, Rough Transcript of Deposition of Gordon Row, dated May 6, 2022, 55 pages.
SHL Medical AG (Inventors: Anders Holmqvist, and Hsueh-Yi Chen) Junior Party (U.S. Appl. No. 17/020,027), v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, SHL Notice of Service of Supplemental Evidence, dated Jun. 7, 2022, 3 pages.
SHL Medical AG (Inventors: Anders Holmqvist, and Hsueh-Yi Chen) Junior Party (U.S. Appl. No. 17/020,027), v. Sanofi-Aventis Deutschland GMBH (Inventors: Yannick Hourmand, Douglas Ivan Jennings, and Matthew Ekman), Senior Party (U.S. Appl. No. 17/020,027), Patent Interference No. 106,135, SHL Updated Exhibit List, dated Jun. 7, 2022, 4 pages.

(56) References Cited

OTHER PUBLICATIONS

*SHL Medical AG (Inventors: Anders Holmqvist, and Hsueh-Yi Chen) Junior Party (U.S. Appl. No. 17/020,027)*, v. *Sanofi-Aventis Deutschland GMBH (Inventors: Yannick Hourmand, Douglas Ivan Jennings, and Matthew Ekman), Senior Party (U.S. Appl. No. 17/020,027)*, Patent Interference No. 106,135, Exhibit 2025: Declaration of Neil Sheehan, dated Jun. 6, 2022, 9 pages.

*SHL Medical AG (Inventors: Anders Holmqvist, and Hsueh-Yi Chen) Junior Party (U.S. Appl. No. 17/020,027)*, v. *Sanofi-Aventis Deutschland GMBH (Inventors: Yannick Hourmand, Douglas Ivan Jennings, and Matthew Ekman), Senior Party (U.S. Appl. No. 17/020,027)*, Patent Interference No. 106,135, Exhibit 2001: Declaration of Neil Sheehan, dated Dec. 15, 2021, 44 pages.

*SHL Medical AG (Inventors: Anders Holmqvist, and Hsueh-Yi Chen) Junior Party (U.S. Appl. No. 17/020,027)*, v. *Sanofi-Aventis Deutschland GMBH (Inventors: Yannick Hourmand, Douglas Ivan Jennings, and Matthew Ekman), Senior Party (U.S. Appl. No. 17/020,027)*, Patent Interference No. 106,135, Decision on Motions, dated Jul. 29, 2022, 40 pages.

\* cited by examiner

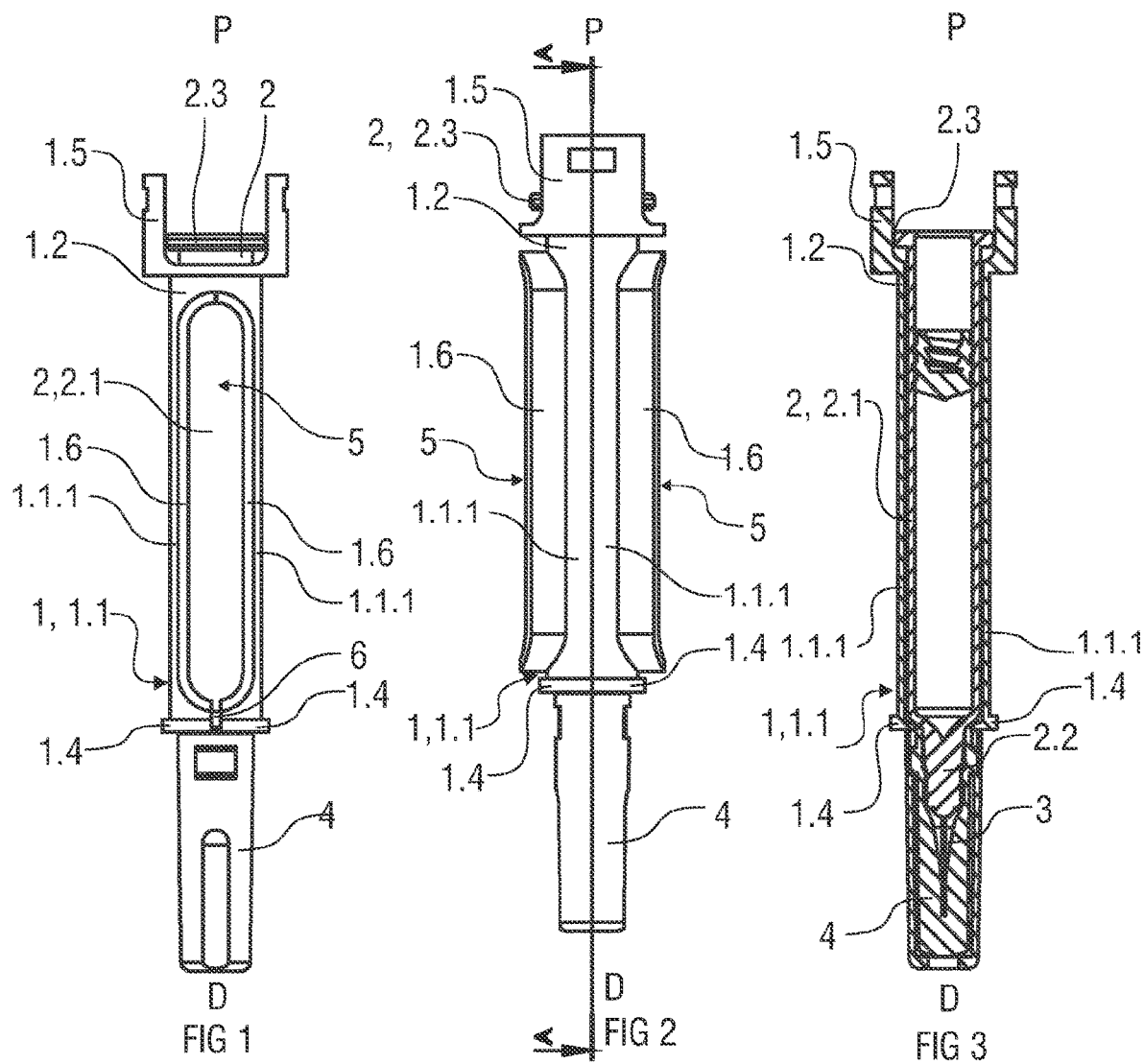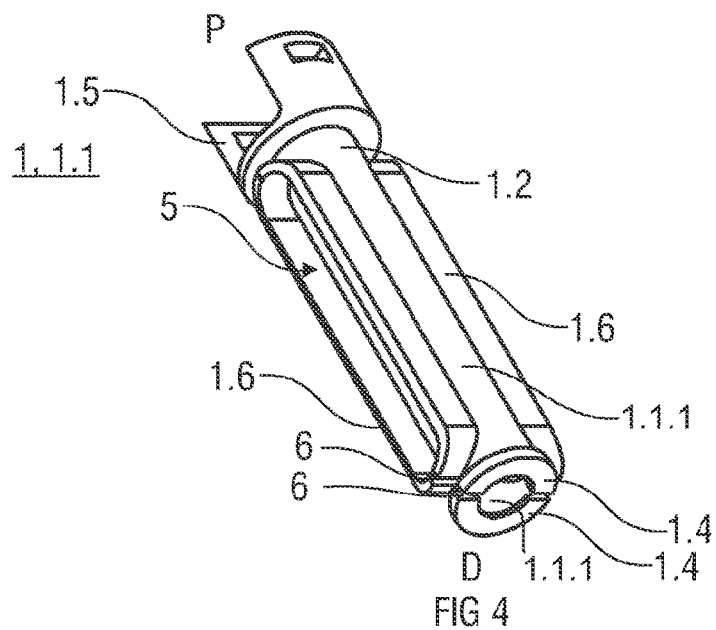

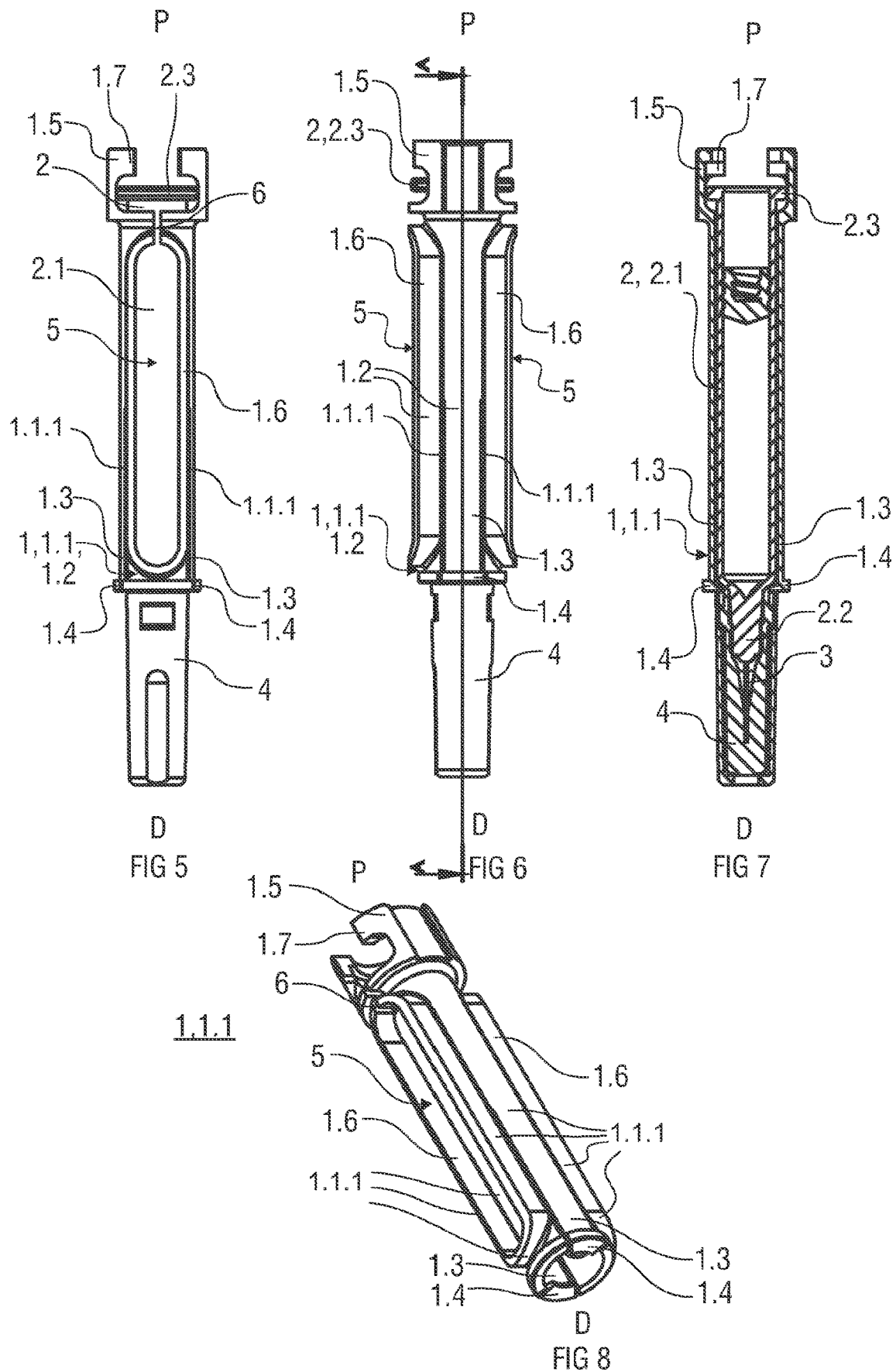

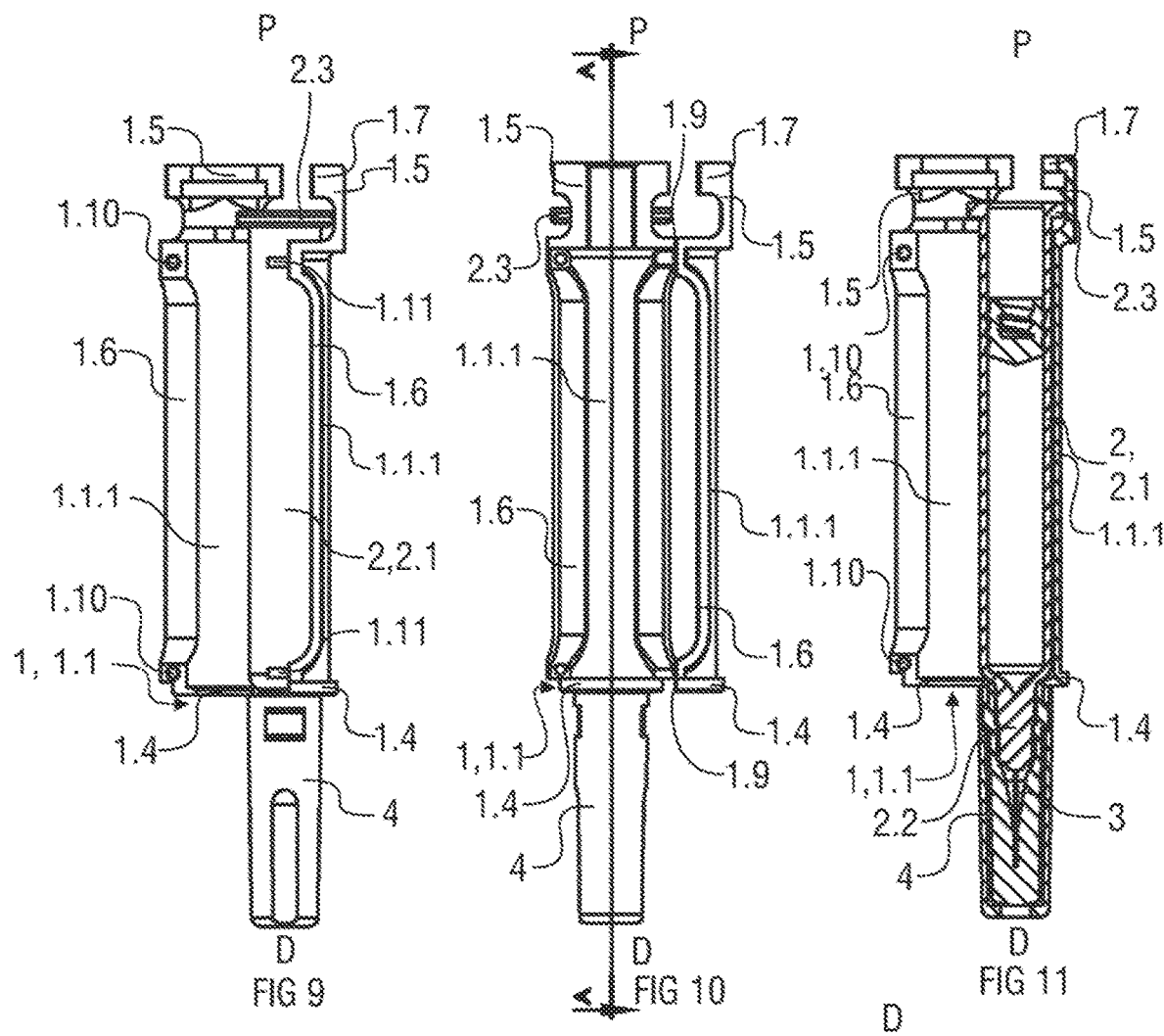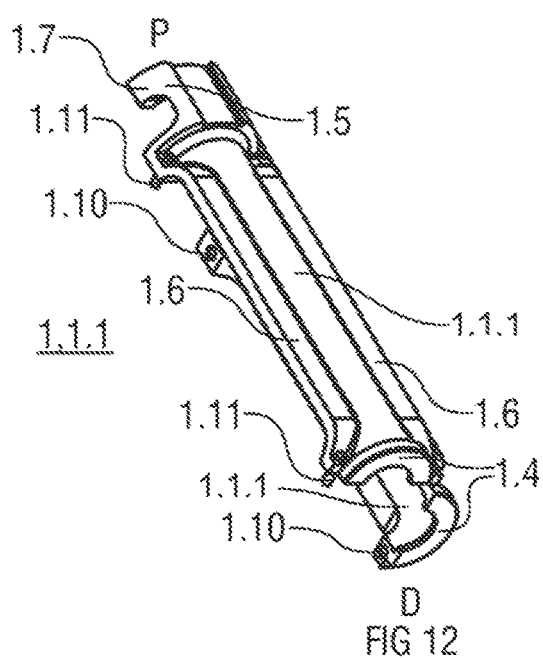

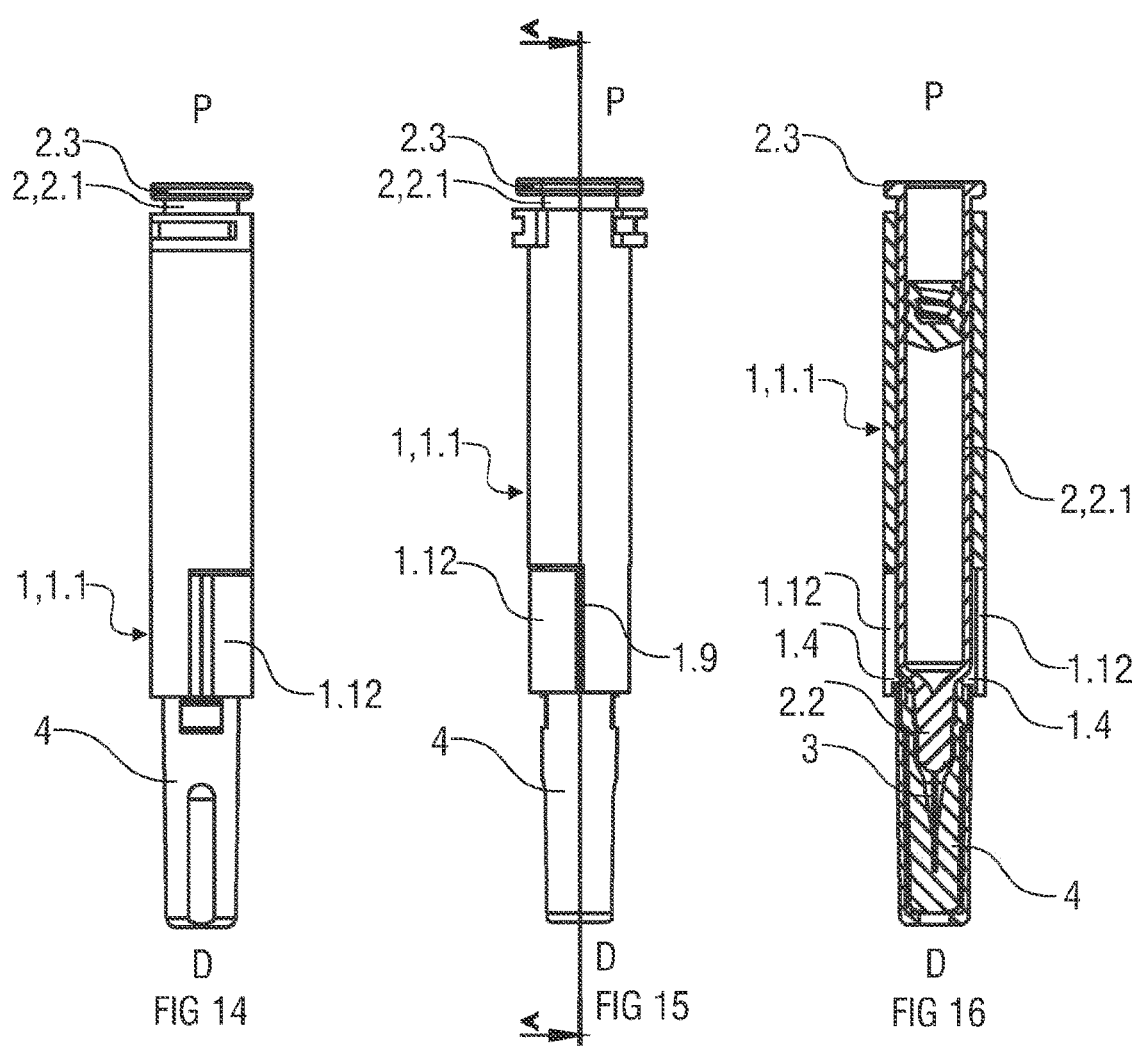
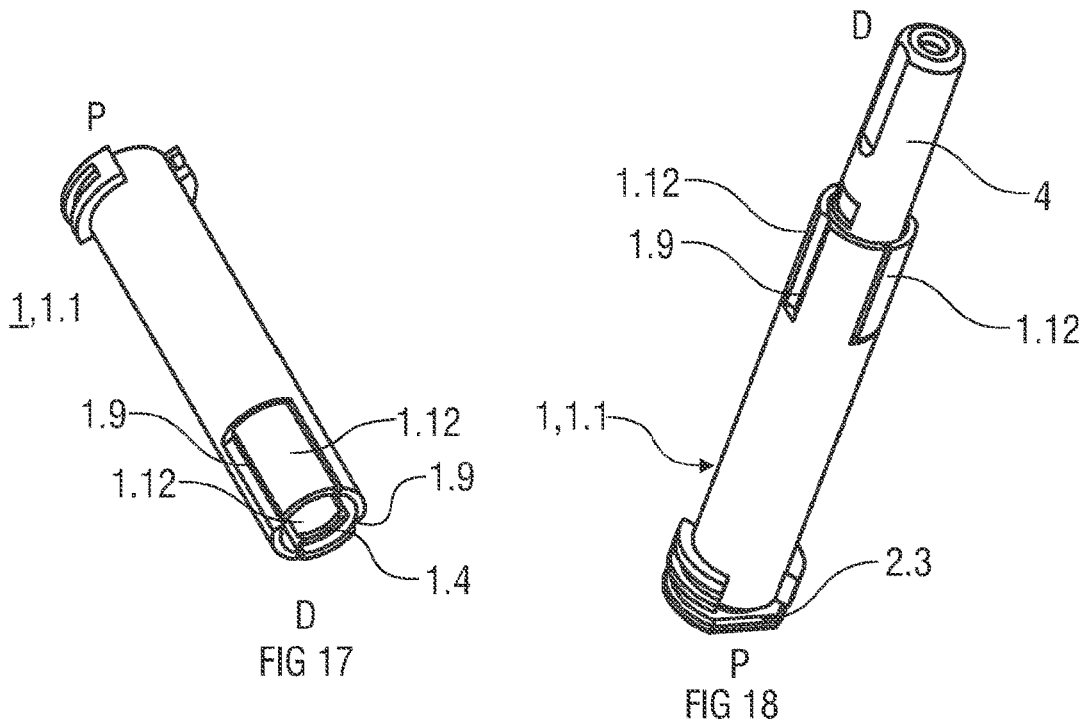

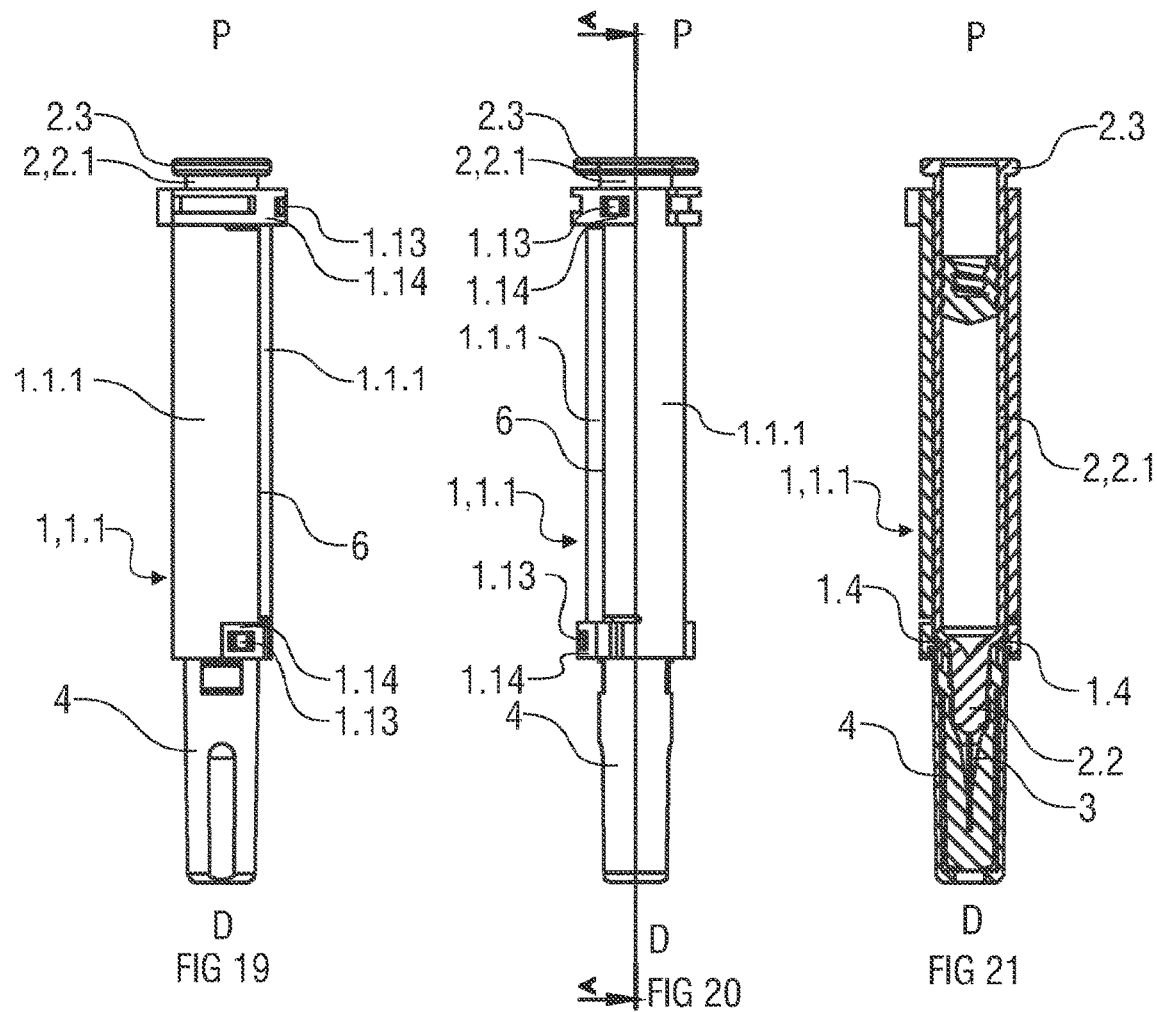
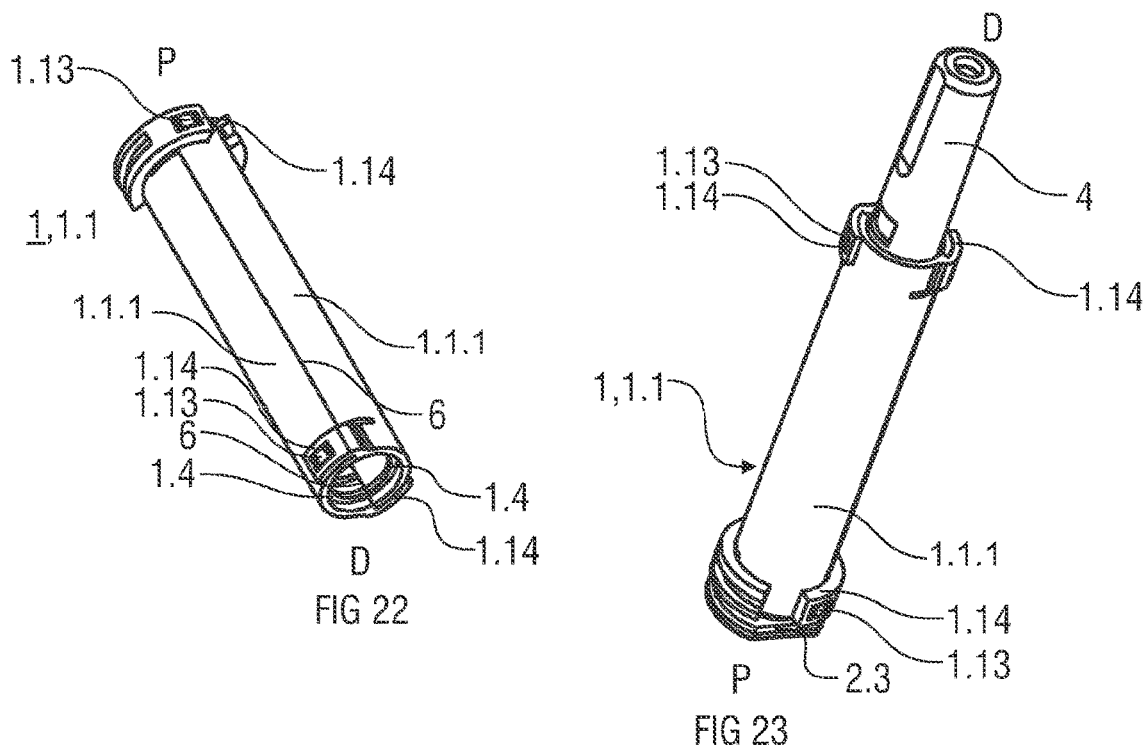

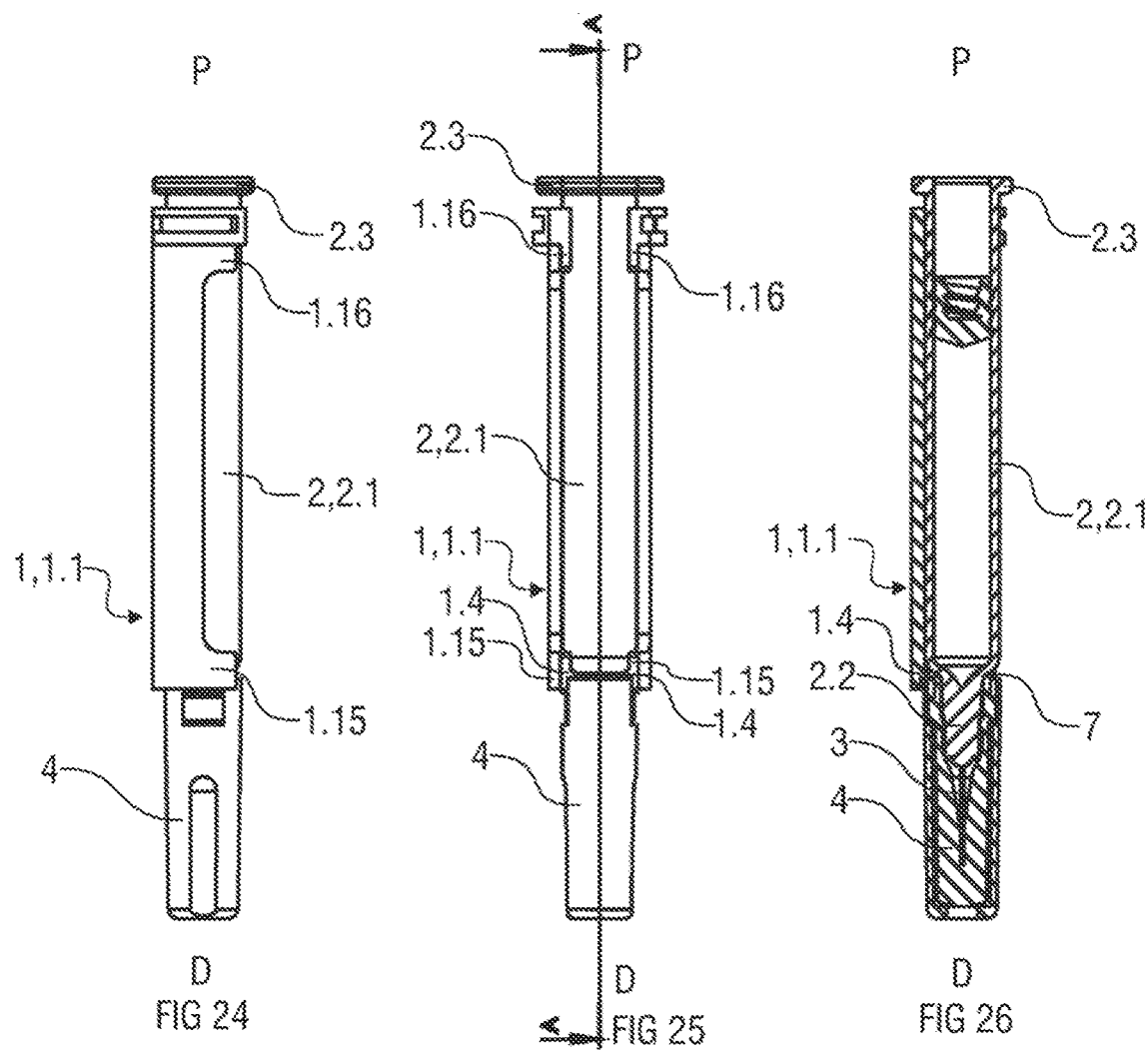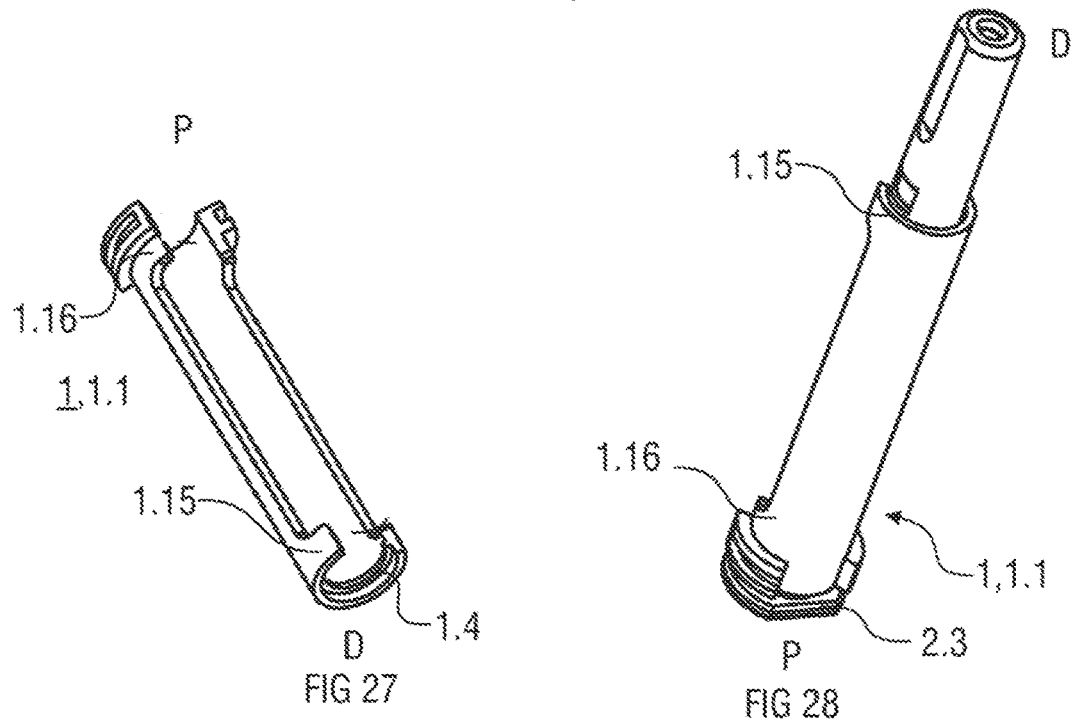

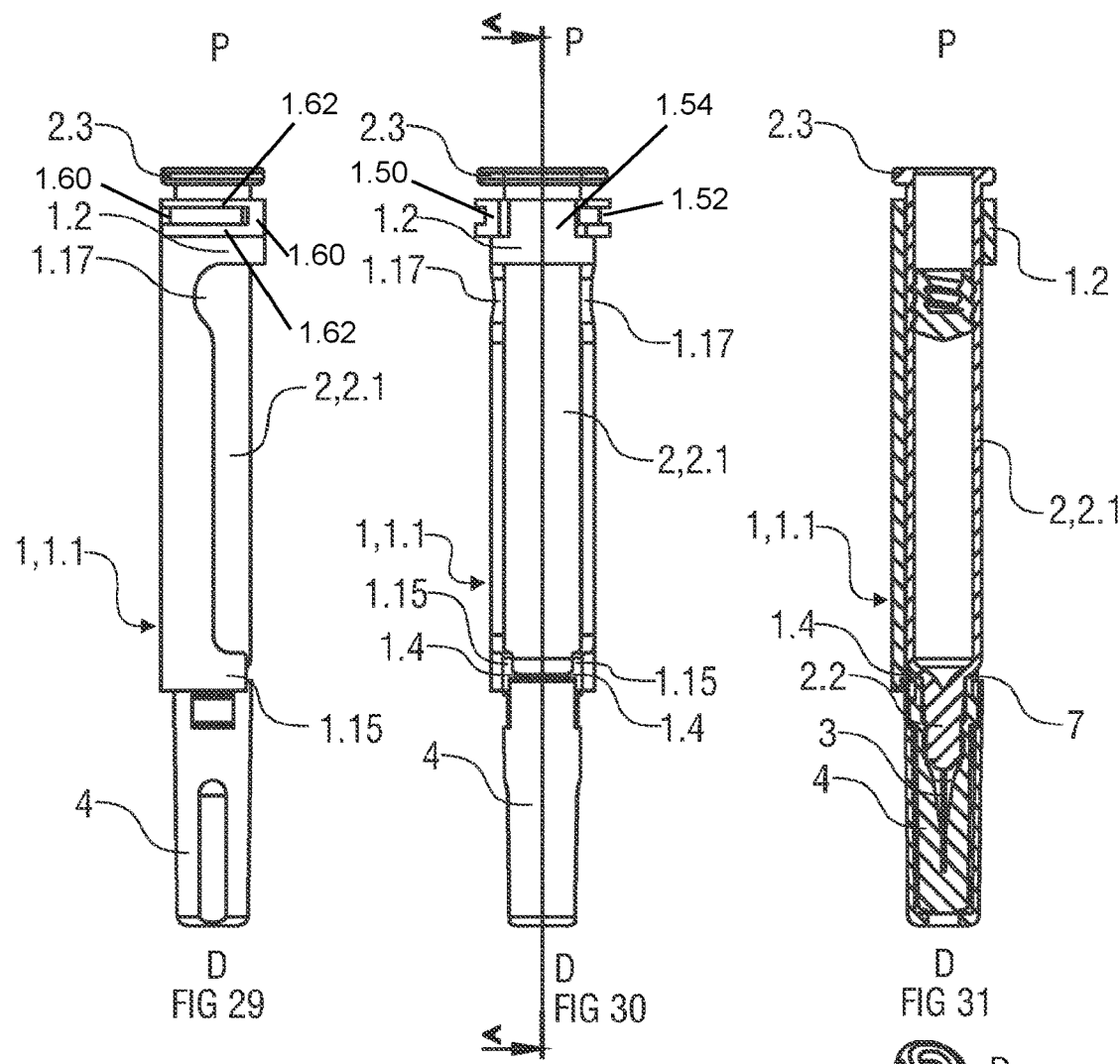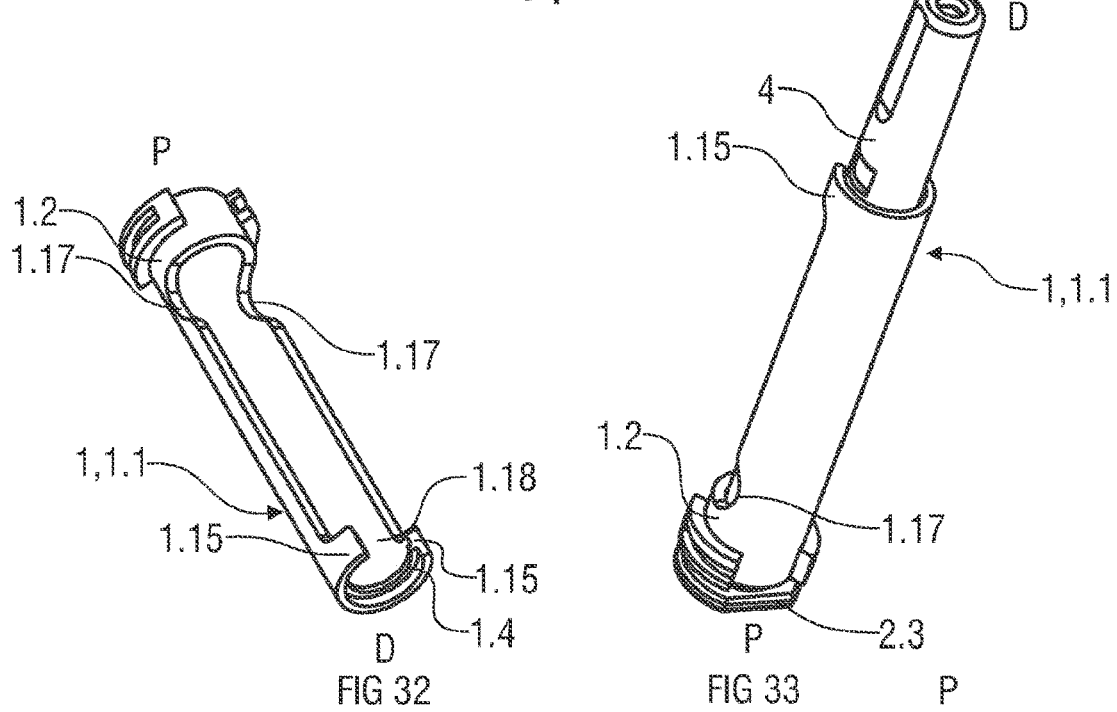

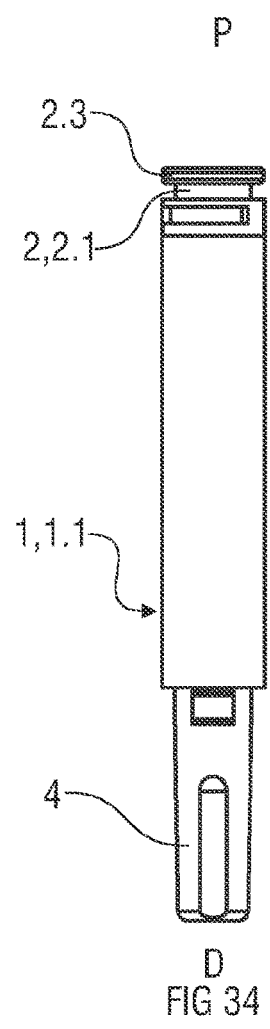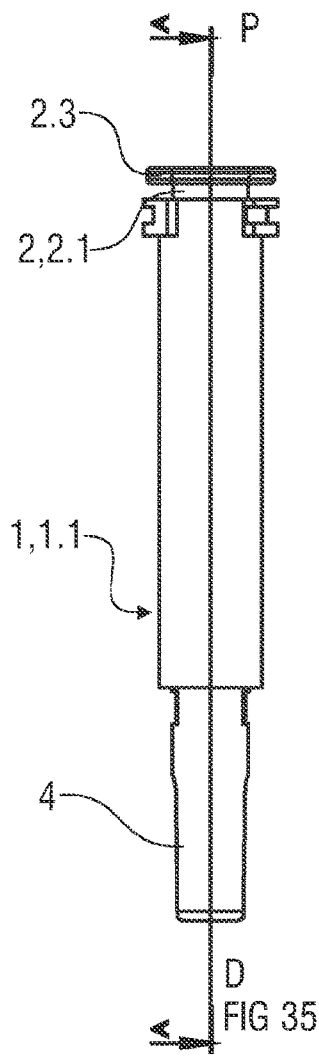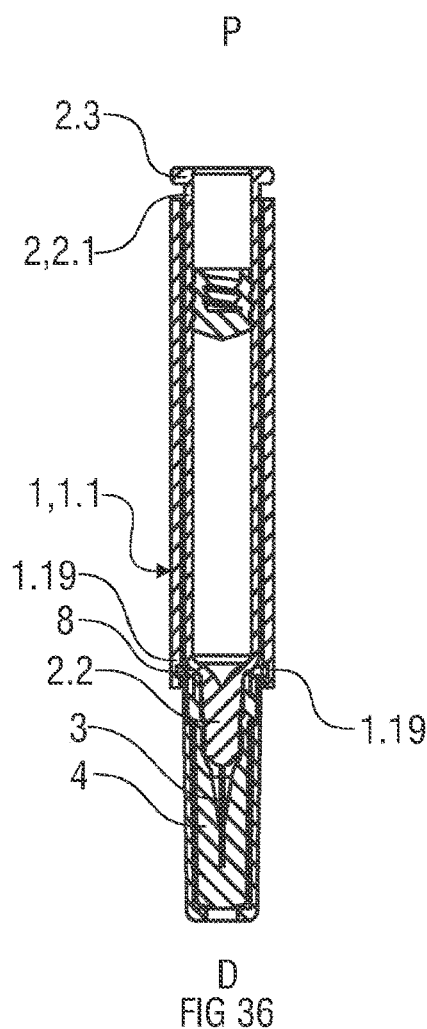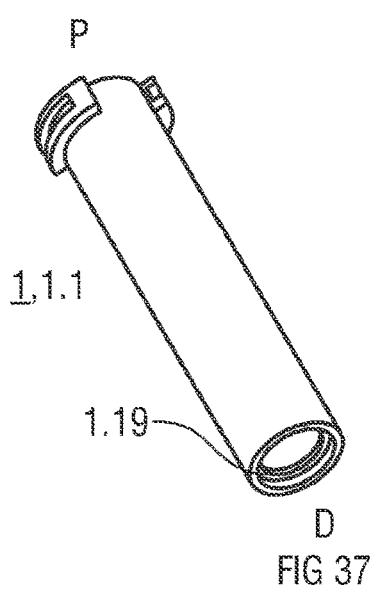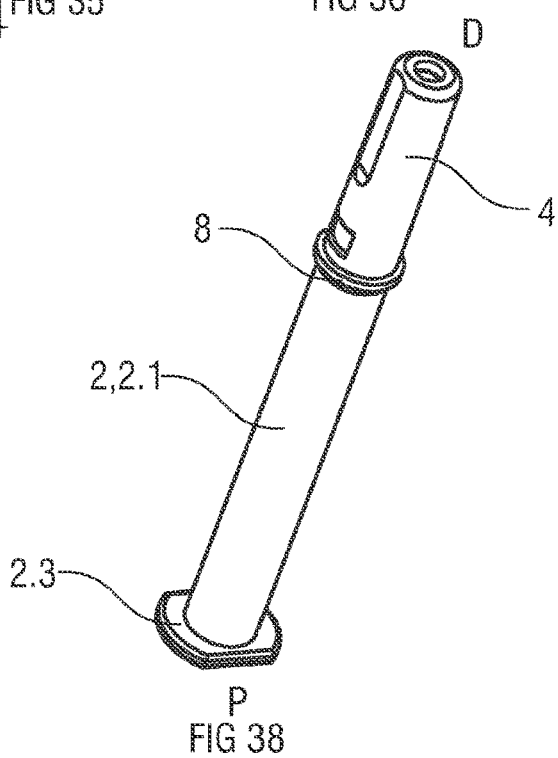

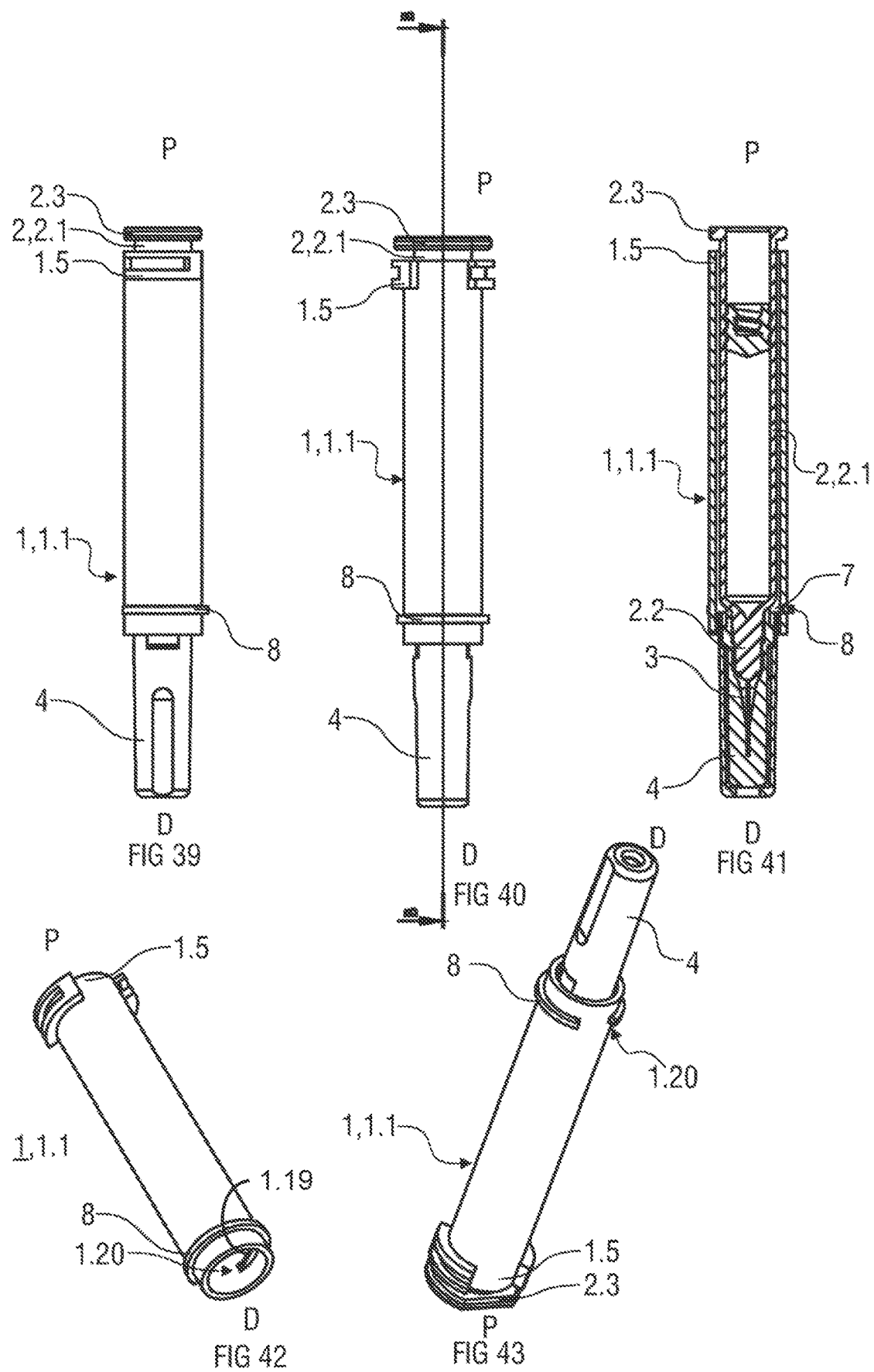

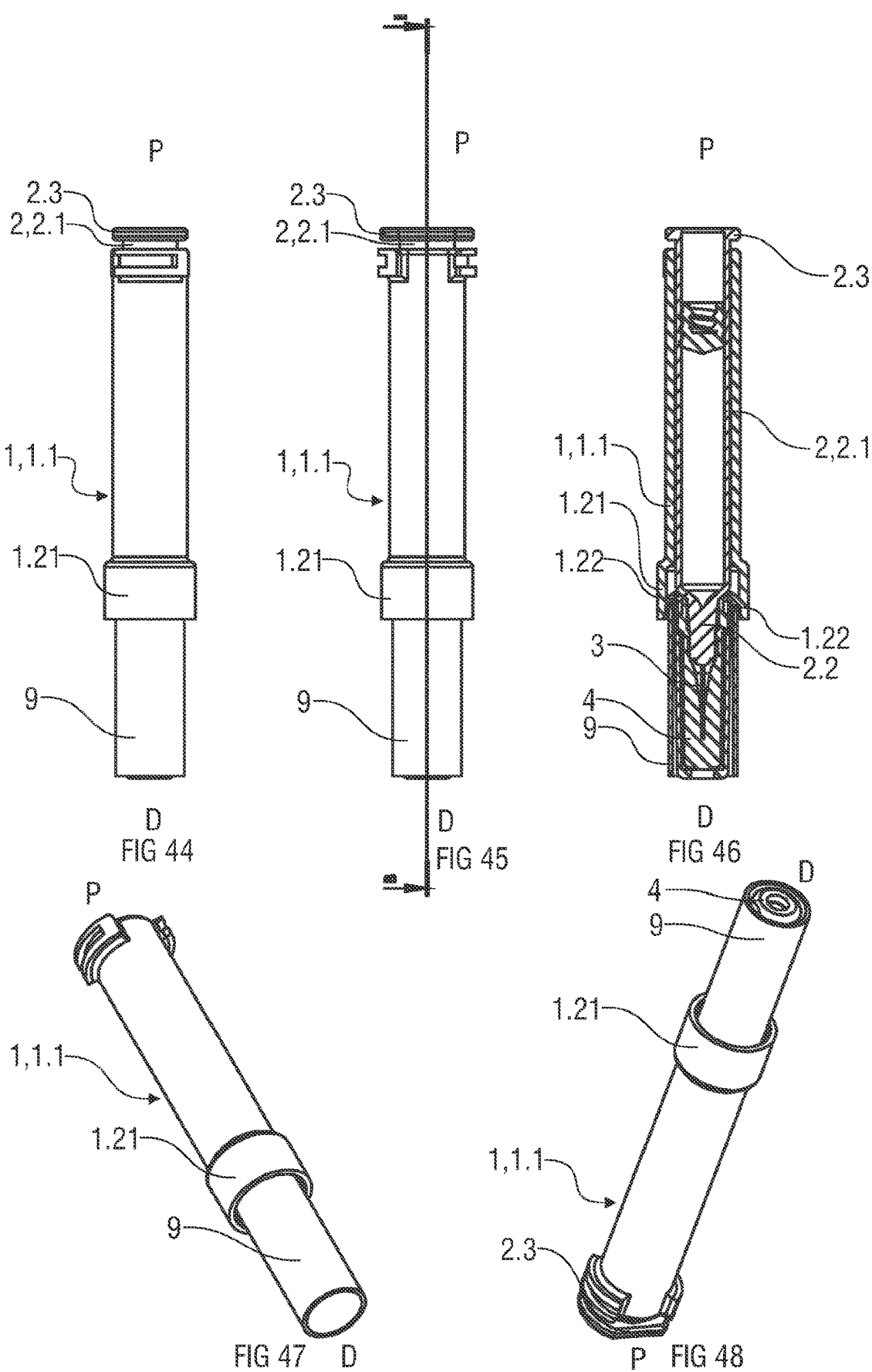

SYRINGE CARRIER

CROSS REFERENCE TO RELATED APPLICATIONS

The present application is a continuation of U.S. patent application Ser. No. 17/020,027, filed Sep. 14, 2020, which is a continuation of U.S. patent application Ser. No. 16/353,282, filed Mar. 14, 2019, which is a continuation of U.S. patent application Ser. No. 15/976,824, filed May 10, 2018, now U.S. Pat. No. 10,646,656, which is a continuation of U.S. patent application Ser. No. 14/362,537, filed Jun. 3, 2014, now U.S. Pat. No. 10,434,258, which is a U.S. National Phase Application pursuant to 35 U.S.C. § 371 of International Application No. PCT/EP2012/074466 filed Dec. 5, 2012, which claims priority to European Patent Application No. 11192585.5 filed Dec. 8, 2011. The entire disclosure contents of these applications are herewith incorporated by reference into the present application.

TECHNICAL FIELD

The invention relates to syringe carrier.

BACKGROUND

In a conventional medicament delivery device (e.g., an autoinjector), a pre-filled syringe is housed in a carrier which is axially movable to achieve needle penetration in an injection site and, optionally, needle withdrawal. A conventional carrier provides shoulders that are adapted to engage a neck on the syringe and prevent the syringe from disengaging the carrier. Because syringes are generally supplied with rigid needle shields covering the needle and those needle shields have a diameter greater than a diameter between the shoulders, a separate assembly step is required—inserting the syringe in the carrier and then attaching the rigid needle shield to the needle. Accordingly, there is a need for a syringe carrier which does not require this separate assembly step.

SUMMARY

It is an object of the present invention to provide an improved syringe carrier.

In an exemplary embodiment, a syringe carrier according to the present invention comprises a body adapted to receive a barrel of a syringe. The body includes two sections having distal ends with shoulder sections adapted to engage a circumferential gap between the barrel of the syringe and a needle shield covering a needle of the syringe.

In an exemplary embodiment, the sections are resiliently coupled to a collar on a proximal end of the body. The shoulder sections deflect when engaged by the needle shield and return to a non-deflected position when disengaged by the needle shield to engage the circumferential gap between the barrel of the syringe and the needle shield.

In an exemplary embodiment, the sections are resiliently coupled to a collar on a distal end of the body. The sections deflect when engaged by the needle shield and return to a non-deflected position when disengaged by the needle shield to engage a finger flange of the syringe. The body includes resilient arms having additional shoulder sections adapted to engage the circumferential gap between the barrel of the syringe and a needle shield covering a needle of the syringe. The arms deflect when engaged by the needle shield and return to a non-deflected position when disengaged by the needle shield to engage the circumferential gap between the barrel of the syringe and a needle shield.

In an exemplary embodiment, the sections are coupled via at least one hinge and are movable between an open position and a closed position. A first section includes a pin adapted to engage a hole on a second section to secure the sections in the closed position.

In an exemplary embodiment, the sections are coupled via at least one clip and are movable between an open position and a closed position. The at least one clip includes a hook on a first section adapted to engage an eye on a second section to secure the sections in the closed position.

In an exemplary embodiment, the sections include doors hingedly coupled to the body and additional shoulder sections are formed on distal ends of the doors.

In an exemplary embodiment, the shoulder sections include proximally-facing contoured surfaces to accommodate a proximal portion of a neck of the syringe and distally-facing planar surfaces to abut the needle shield.

In an exemplary embodiment, the body includes one or more viewing windows.

In an exemplary embodiment, the body includes a retainer element adapted to provide an abutment surface to prevent the syringe from disengaging the syringe carrier in a proximal direction.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 1 is a top view of an exemplary embodiment of a syringe carrier according to the present invention, FIG. 2 is a lateral view of the syringe carrier of FIG. 1, FIG. 3 is a longitudinal section of the syringe carrier of FIG. 1 in the section plane A-A, FIG. 4 is a perspective view of the syringe carrier of FIG. 1, FIG. 5 is a top view of another exemplary embodiment of a syringe carrier according to the present invention, FIG. 6 is a lateral view of the syringe carrier of FIG. 5, FIG. 7 is a longitudinal section of the syringe carrier of FIG. 5 in the section plane A-A, FIG. 8 is a perspective view of the syringe carrier of FIG. 5, FIG. 9 is a top view of yet another exemplary embodiment of a syringe carrier according to the present invention, FIG. 10 is a lateral view of the syringe carrier of FIG. 9, FIG. 11 is a longitudinal section of the syringe carrier of FIG. 9 in the section plane A-A, FIG. 12 is a perspective view of the syringe carrier of FIG. 9, FIG. 13 is another perspective view of the syringe carrier of FIG. 9 with a syringe inserted, FIG. 14 is a top view of yet another exemplary embodiment of a syringe carrier according to the present invention, FIG. 15 is a lateral view of the syringe carrier of FIG. 14, FIG. 16 is a longitudinal section of the syringe carrier of FIG. 14 in the section plane A-A, FIG. 17 is a perspective view of the syringe carrier of FIG. 14, FIG. 18 is another perspective view of the syringe carrier of FIG. 14 with a syringe inserted, FIG. 19 is a top view of yet another exemplary embodiment of a syringe carrier according to the present invention, FIG. 20 is a lateral view of the syringe carrier of FIG. 19, FIG. 21 is a longitudinal section of the syringe carrier of FIG. 19 in the section plane A-A, FIG. 22 is a perspective view of the syringe carrier of FIG. 19, FIG. 23 is another perspective view of the syringe carrier of FIG. 19 with a syringe inserted, FIG. 24 is a top view of yet another exemplary embodiment of a syringe carrier according to the present invention, FIG. 25 is a lateral view of the syringe carrier of FIG. 24, FIG. 26 is a longitudinal section of the syringe carrier of FIG. 24 in the section plane A-A, FIG. 27 is a perspective view of the syringe carrier of FIG. 24, FIG. 28 is another perspective view of the syringe carrier of FIG. 24 with a syringe inserted, FIG. 29 is a top view of yet another exemplary embodiment of a syringe carrier according to the present invention, FIG. 30 is a lateral view of the syringe carrier of FIG. 29, FIG. 31 is a longitudinal section of the syringe carrier of FIG. 29 in the section plane A-A, FIG. 32 is a perspective view of the syringe carrier of FIG. 29, FIG. 33 is another perspective view of the syringe carrier of FIG. 29 with a syringe inserted, FIG. 34 is a top view of yet another exemplary embodiment of a syringe carrier according to the present invention, FIG. 35 is a lateral view of the syringe carrier of FIG. 34, FIG. 36 is a longitudinal section of the syringe carrier of FIG. 34 in the section plane A-A, FIG. 37 is a perspective view of the syringe carrier of FIG. 34, FIG. 38 is another perspective view of the syringe carrier of FIG. 34 with a syringe inserted, FIG. 39 is a top view of yet another exemplary embodiment of a syringe carrier according to the present invention, FIG. 40 is a lateral view of the syringe carrier of FIG. 39, FIG. 41 is a longitudinal section of the syringe carrier of FIG. 39 in the section plane B-B, FIG. 42 is a perspective view of the syringe carrier of FIG. 39, FIG. 43 is another perspective view of the syringe carrier of FIG. 39 with a syringe inserted, FIG. 44 is a top view of yet another exemplary embodiment of a syringe carrier according to the present invention, FIG. 45 is a lateral view of the syringe carrier of FIG. 44, FIG. 46 is a longitudinal section of the syringe carrier of FIG. 44 in the section plane B-B, FIG. 47 is a perspective view of the syringe carrier of FIG. 44, and FIG. 48 is another perspective view of the syringe carrier of FIG. 44 with a syringe inserted.

Corresponding parts are marked with the same reference symbols in all figures.

DETAILED DESCRIPTION

Generally, and applicable to all exemplary embodiments of the present invention, the syringe 2 comprises a barrel 2.1 and a neck 2.2 which has a smaller diameter than the barrel 2.1. A needle 3 is mounted to the neck 2.2 and a rigid needle shield (RNS) 4 is removably arranged on the needle 3. When coupled to the needle 3, a portion of the RNS may cover a portion of the neck 2.2, leaving a circumferential gap between the barrel 2.1 and the RNS 4. The RNS 4 has a diameter substantially equal to the diameter of the barrel 2.1.

FIGS. 1-4 show a first exemplary embodiment of a syringe carrier 1 according to the present in invention. FIG. 1 is a top view of the syringe carrier 1 for supporting a syringe 2. FIG. 2 is a lateral view of the syringe carrier of FIG. 1. FIG. 3 is a longitudinal section of the syringe carrier of FIG. 1 in the section plane A-A. FIG. 4 is a perspective view of the syringe carrier of FIG. 1 without the syringe 2.

As shown in FIGS. 1-4, the syringe carrier 1 comprises an elongate body 1.1 arranged to receive the barrel 2.1. In this exemplary embodiment, the body 1.1 has a cylindrical shape with an internal diameter corresponding to the diameter of the barrel 2.1. The body 1.1 comprises a collar 1.2 at a proximal end dimensioned to allow axial insertion of the syringe 2 into the syringe carrier 1 in a distal direction D. Resilient sections 1.1.1 extend distally from the collar 1.2. Distal ends of the sections 1.1.1 include shoulder sections 1.4 shaped as portions of a circle arranged in a transverse plane with respect to a longitudinal axis of the carrier 1. The shoulder sections include facing surfaces 6. When the sections 1.1.1 are in a non-deflected position, the facing surfaces 6 may abut each other, and the shoulder sections 1.4 form a circular shoulder (because the facing surfaces 6 abut each other) adapted to engage the circumferential gap between the barrel 2.1 and the RNS 4.

The syringe 2, with RNS 4 attached to the needle 3, may be loaded into the syringe carrier 1 by sliding the syringe 2 in the distal direction D into the syringe carrier 2. When the RNS 4 abuts the shoulder sections 1.4, additional axial force may be applied to cause the arms 1.3 to deflect radially. When the RNS 4 has bypassed the shoulder sections 1.4, the sections 1.1.1 may return to the non-deflected position, and the shoulder sections 1.4 may engage the circumferential gap between the barrel 2.1 and the RNS 4 and prevent the syringe 2 from moving in the distal direction D relative to the syringe carrier 1.

In an exemplary embodiment, the proximal end 1.5 of the body 1.1 may be arranged to receive a finger flange 2.3 of the syringe 2.

In an exemplary embodiment, the shoulder sections 1.4 may include proximally-facing contoured surfaces to accommodate a proximal portion of the neck 2.2 of the syringe 2 and distally-facing planar surfaces to abut the RNS 4.

In an exemplary embodiment, viewing windows 5 may be arranged in the body 1.1 for allowing visual access to the barrel 2.1 of the syringe 2 when the syringe 2 is in the syringe carrier 2. In an exemplary embodiment, the windows 5 are formed when cut-outs in the arms 1.3 are substantially contiguous when the arms 1.3 are in the non-deflected position (as shown in FIG. 1). A projection 1.6 may be formed around each cut-out, and when the sections 1.1.1 are in the non-deflected position, the projections 1.6 may form an outline for the window 5. In another exemplary embodiment, the windows 5 may be formed in the sections 1.1.1.

FIGS. 5-8 show a second exemplary embodiment of a syringe carrier 1 according to the present invention. FIG. 6 is a lateral view of the syringe carrier 1 of FIG. 5. FIG. 7 is a longitudinal section of the syringe carrier 1 of FIG. 5 in the section plane A-A. FIG. 8 is a perspective view of the syringe carrier of FIG. 5 without the syringe 2.

As shown in FIGS. 5-8, the syringe carrier 1 comprises an elongate body 1.1 arranged to receive the barrel 2.1. In this exemplary embodiment, the body 1.1 is comprised of two resilient sections 1.1.1 which, when together, have a cylindrical shape with an internal diameter corresponding to the diameter of the barrel 2.1. Distal ends of the sections 1.1.1 of the body 1.1 comprise part of a collar 1.2 dimensioned to allow axial insertion of the syringe 2 into the syringe carrier 1. Resilient arms 1.3 are formed in the body 1.1. Distal ends of the arms 1.3 include shoulder sections 1.4 shaped as portions of a circle arranged in a transverse plane with respect to a longitudinal axis of the carrier 1. The shoulder sections include facing surfaces 6. When the arms 1.3 are in a non-deflected position, the facing surfaces 6 may abut the distal ends of the sections 1.1.1 of the body 1.1 to form a circular shoulder adapted to engage the circumferential gap between the barrel 2.1 and the RNS 4.

The syringe 2, with RNS 4 attached to the needle 3, may be loaded into the syringe carrier 1 by sliding the syringe 2 in the distal direction D into the syringe carrier 2. When the RNS 4 abuts proximal ends of the sections 1.1.1, the sections 1.1.1 may deflect radially. When the RNS 4 has bypassed the proximal ends of the section 1.1.1, the sections 1.1.1 may return to the non-deflected position. When the RNS 4 abuts the shoulder sections 1.4, the arms 1.3 may deflect until the RNS 4 bypasses the shoulder sections 1.4. Then, the arms 1.3 may return to the non-deflected position, and the shoulder sections 1.4 and the collar 1.2 may engage the circumferential gap between the barrel 2.1 and the RNS 4 and prevent the syringe 2 from moving in the distal direction D relative to the syringe carrier 1.

In an exemplary embodiment, the proximal end 1.5 of the body 1.1 may be arranged to receive a finger flange 2.3 of the syringe 2. The proximal end 1.5 may also include a retainer element 1.7 which is adapted to provide an abutment surface to prevent the syringe 2 from disengaging the syringe carrier 1 in the proximal direction P.

In an exemplary embodiment, the shoulder sections 1.4 may include proximally-facing contoured surfaces to accommodate a proximal portion of the neck 2.2 of the syringe 2 and distally-facing planar surfaces to abut the RNS 4.

In an exemplary embodiment, viewing windows 5 may be arranged in the body 1.1 for allowing visual access to the barrel 2.1 of the syringe 2 when the syringe 2 is in the syringe carrier 2. In an exemplary embodiment, the windows 5 are formed when cut-outs in the sections 1.1.1 are substantially contiguous when the sections 1.1.1 are in the non-deflected position (as shown in FIG. 5). A projection 1.6 may be formed around each cut-out, and when the sections 1.1.1 are in the non-deflected position, the projections 1.6 may form an outline for the window 5.

FIGS. 9-13 show a third exemplary embodiment of a syringe carrier 1 according to the present invention. FIG. 9 is a top view of a third embodiment of a syringe carrier 1 for supporting a syringe 2. FIG. 10 is a lateral view of the syringe carrier 1 of FIG. 9. FIG. 11 is a longitudinal section of the syringe carrier 1 of FIG. 9 in the section plane A-A. FIG. 12 is a perspective view of the syringe carrier of FIG. 9 without the syringe 2. FIG. 13 is another perspective view of the syringe carrier of FIG. 9.

As shown in FIGS. 9-13, the syringe carrier 1 comprises an elongate body 1.1 arranged to receive the barrel 2.1. In this exemplary embodiment, the body 1.1 is comprised of two sections 1.1.1 which, when together, have a cylindrical shape with an internal diameter corresponding to the diameter of the barrel 2.1. The sections 1.1.1 may be coupled by a side hinge which allows the section 1.1.1 to rotate relative to each other sufficient to receive the syringe 2. Proximal and distal ends of the sections 1.1.1 include shoulder sections 1.4 shaped as portions of a circle arranged in a transverse plane with respect to a longitudinal axis of the carrier 1. The shoulder sections include facing surfaces 6. When the sections 1.1.1 are in a closed position, the facing surfaces 6 may abut each other so that the shoulder sections 1.4 form circular shoulders adapted to proximally abut a finger flange 2.3 on the syringe 2 and to distally engage the circumferential gap between the barrel 2.1 and the RNS 4. The facing surfaces 6 of one section 1.1.1 may include holes 1.10 and the facing surfaces 6 of the other section 1.1.1 may include pins 1.11 adapted to engage (e.g., frictionally, snap-fit, etc.) the holes 1.10 to secure the sections 1.1.1 in the closed position.

The syringe 2, with RNS 4 attached to the needle 3, may be loaded into the syringe carrier 1 by opening the sections 1.1.1 about the hinge and placing the syringe 2 in the syringe carrier 2. When the sections 1.1.1 are closed, the pins 1.11 engage the holes 1.10, and the proximal shoulder sections 1.4 form circular shoulders adapted to proximally abut a finger flange 2.3 on the syringe 2 and the distal shoulder section s1.4 to distally engage the circumferential gap between the barrel 2.1 and the RNS 4. Thus, the syringe 2 is prevented from moving axially relative to the syringe carrier 1.

In an exemplary embodiment, the proximal end 1.5 may include a retainer element 1.7 which is adapted to provide an abutment surface to prevent the syringe 2 from disengaging the syringe carrier 1 in the proximal direction P.

In an exemplary embodiment, the shoulder sections 1.4 may include proximally-facing contoured surfaces to accommodate a proximal portion of the neck 2.2 of the syringe 2 and distally-facing planar surfaces to abut the RNS 4.

In an exemplary embodiment, viewing windows 5 may be arranged in the body 1.1 for allowing visual access to the barrel 2.1 of the syringe 2 when the syringe 2 is in the syringe carrier 2. In an exemplary embodiment, the windows 5 are formed when cut-outs in the sections 1.1.1 are substantially contiguous when the sections 1.1.1 are in the closed position. A projection 1.6 may be formed around each cut-out, and when the sections 1.1.1 are in the non-deflected position, the projections 1.6 may form an outline for the window 5.

FIGS. 14-18 show a fourth exemplary embodiment of a syringe carrier 1 according to the present invention. FIG. 14 is a top view of a fourth embodiment of a syringe carrier 1 for supporting a syringe 2. FIG. 15 is a lateral view of the syringe carrier 1 of FIG. 14. FIG. 16 is a longitudinal section of the syringe carrier 1 of FIG. 14 in the section plane A-A. FIG. 17 is a perspective view of the syringe carrier of FIG. 14 without the syringe 2. FIG. 18 is another perspective view of the syringe carrier of FIG. 14.

As shown in FIGS. 14-18, the syringe carrier 1 comprises an elongate body 1.1 arranged to receive the barrel 2.1. In this exemplary embodiment, the body 1.1 has a cylindrical shape with an internal diameter corresponding to the diameter of the barrel 2.1. A distal end of the body 1.1 includes a shoulder sections 1.4 shaped as a portion of a circle arranged in a transverse plane with respect to a longitudinal axis of the carrier 1, and at least one door 1.12 hingedly coupled to the body 1.1 and including a shoulder section 1.4. A hinge 1.9 coupling the door 1.12 to the body 1.1 may be provided on an axis parallel to the longitudinal axis of the syringe carrier 1 or on an axis transverse to the longitudinal axis of the syringe carrier 1. The shoulder section 1.4 includes facing surfaces 6 which abut facing surfaces 6 of the door 1.12 when the door 1.12 is in a closed position (as shown in FIG. 14). When the door 1.12 is in the closed position, the facing surfaces 6 may abut each other so that the shoulder sections 1.4 on the body 1.1 and the door 1.12 to form a circular shoulder adapted to engage the circumferential gap between the barrel 2.1 and the RNS 4. The facing surfaces 6 of the door 1.12 may include holes 1.10 and the facing surfaces 6 of the body 1.1 may include pins 1.11 (or vice-versa) adapted to engage (e.g., frictionally, snap-fit, etc.) the holes 1.10 to secure the door 1.12 in the closed position.

The syringe 2, with RNS 4 attached to the needle 3, may be loaded into the syringe carrier 1 by opening the door 1.12 and sliding the syringe 2 into the syringe carrier 1. When the circumferential gap between the barrel 2.1 and the RNS 4 engages the shoulder section 1.4 on the body 1.1, the door 1.12 may be closed to engage the gap and prevent the syringe 2 from moving axially relative to the syringe carrier 1.

In an exemplary embodiment, the shoulder sections 1.4 may include proximally-facing contoured surfaces to accommodate a proximal portion of the neck 2.2 of the syringe 2 and distally-facing planar surfaces to abut the RNS 4.

In an exemplary embodiment, viewing windows (not shown) may be arranged in the body 1.1 for allowing visual access to the barrel 2.1 of the syringe 2 when the syringe 2 is in the syringe carrier 2. In an exemplary embodiment, the windows are formed as cut-outs.

FIGS. 19-23 show a fifth exemplary embodiment of a syringe carrier 1 according to the present invention. FIG. 19 is a top view of a fifth embodiment of a syringe carrier 1 for supporting a syringe 2. FIG. 20 is a lateral view of the syringe carrier 1 of FIG. 19. FIG. 21 is a longitudinal section of the syringe carrier 1 of FIG. 19 in the section plane A-A. FIG. 22 is a perspective view of the syringe carrier of FIG. 19 without the syringe 2. FIG. 23 is another perspective view of the syringe carrier of FIG. 19.

As shown in FIGS. 19-23, the syringe carrier 1 comprises an elongate body 1.1 arranged to receive the barrel 2.1. In this exemplary embodiment, the body 1.1 is comprised of two sections 1.1.1 which, when together, have a cylindrical shape with an internal diameter corresponding to the diameter of the barrel 2.1. The sections 1.1.1 may be coupled together by clips. In an exemplary embodiment, a clip may comprise a eye 1.14 on a first section adapted to engage a hook 1.13 on a second section. The eye 1.14 may have a cross-section substantially equal to the cross-section of the hook 1.13 such that the eye 1.14 and hook 1.13 engage in a snap-fit. Distal ends of the sections 1.1.1 include shoulder sections 1.4 shaped as portions of a circle arranged in a transverse plane with respect to a longitudinal axis of the carrier 1. The shoulder sections include facing surfaces 6. When the sections 1.1.1 are in a closed position, the facing surfaces 6 may abut each other so that the shoulder sections 1.4 form circular shoulders adapted engage the circumferential gap between the barrel 2.1 and the RNS 4. Those of skill in the art will understand that the sections 1.1.1 may be hingedly connected.

The syringe 2, with RNS 4 attached to the needle 3, may be loaded into the syringe carrier 1 by opening the sections 1.1.1 and placing the syringe 2 in the syringe carrier 2. When the sections 1.1.1 are closed, the eyes 1.14 engage the hooks 1.13 and the shoulder sections 1.4 engage the circumferential gap between the barrel 2.1 and the RNS 4. Thus, the syringe 2 is prevented from moving axially relative to the syringe carrier 1.

In an exemplary embodiment, the proximal end may include a retainer element which is adapted to provide an abutment surface to prevent the syringe 2 from disengaging the syringe carrier 1 in the proximal direction P.

In an exemplary embodiment, the shoulder sections 1.4 may include proximally-facing contoured surfaces to accommodate a proximal portion of the neck 2.2 of the syringe 2 and distally-facing planar surfaces to abut the RNS 4.

In an exemplary embodiment, viewing windows may be arranged in the body 1.1 for allowing visual access to the barrel 2.1 of the syringe 2 when the syringe 2 is in the syringe carrier 2.

FIGS. 24-28 show a sixth exemplary embodiment of a syringe carrier 1 according to the present invention. FIG. 24 is a top view of a sixth embodiment of a syringe carrier 1 for supporting a syringe 2. FIG. 25 is a lateral view of the syringe carrier 1 of FIG. 24. FIG. 26 is a longitudinal section of the syringe carrier 1 of FIG. 24 in the section plane A-A. FIG. 27 is a perspective view of the syringe carrier of FIG. 24 without the syringe 2. FIG. 28 is another perspective view of the syringe carrier of FIG. 24.

As shown in FIGS. 24-28, the syringe carrier 1 comprises an elongate body 1.1 arranged to receive the barrel 2.1. In this exemplary embodiment, the body 1.1 has a partially cylindrical shape with an internal diameter corresponding to the diameter of the barrel 2.1. The body 1.1 may include a longitudinal slot (e.g., a cut-out) which is adapted to snap over the barrel 2.1 of the syringe 2. Proximal and distal ends of the body 1.1 include clamps 1.15, 1.16 which are adapted to retain the syringe 2 when in the syringe carrier 1. The distal end of the body 1 further includes shoulder sections 1.4 shaped as a portion of a circle arranged in a transverse plane with respect to a longitudinal axis of the carrier 1. The shoulder sections 14 form circular shoulders adapted to engage the circumferential gap between the barrel 2.1 and the RNS 4.

The syringe 2, with RNS 4 attached to the needle 3, may be loaded into the syringe carrier 1 by pressing the barrel 2.1 against the clamps 1.15, 1.16, causing the clamps 1.15, 1.16 to deflect and widen the longitudinal slot in the body 1.1. When the barrel 2.1 bypasses the clamps 1.15, 1.16, the clamps 1.15, 1.16 return to their non-deflected position and retain the syringe 2 in the syringe carrier 1. The shoulder sections 1.4 engage the circumferential gap between the barrel 2.1 and the RNS 4. Thus, the syringe 2 is prevented from moving axially relative to the syringe carrier 1.

In an exemplary embodiment, the proximal end may include a retainer element which is adapted to provide an abutment surface to prevent the syringe 2 from disengaging the syringe carrier 1 in the proximal direction P.

In an exemplary embodiment, the shoulder sections 1.4 may include proximally-facing contoured surfaces to accommodate a proximal portion of the neck 2.2 of the syringe 2 and distally-facing planar surfaces to abut the RNS 4.

In an exemplary embodiment, a viewing window may be arranged in the body 1.1 for allowing visual access to the barrel 2.1 of the syringe 2 when the syringe 2 is in the syringe carrier 2.

FIGS. 29-33 show a seventh exemplary embodiment of a syringe carrier 1 according to the present invention. FIG. 29 is a top view of a seventh embodiment of a syringe carrier 1 for supporting a syringe 2. FIG. 30 is a lateral view of the syringe carrier 1 of FIG. 29. FIG. 31 is a longitudinal section of the syringe carrier 1 of FIG. 29 in the section plane A-A. FIG. 32 is a perspective view of the syringe carrier of FIG. 29 without the syringe 2. FIG. 33 is another perspective view of the syringe carrier of FIG. 29.

As shown in FIGS. 29-33, the syringe carrier 1 comprises an elongate body 1.1 arranged to receive the barrel 2.1. In this exemplary embodiment, the body 1.1 has a partially cylindrical shape with an internal diameter corresponding to the diameter of the barrel 2.1. The body 1.1 includes a collar 1.2 at its proximal end and may include a longitudinal slot (e.g., a cut-out) formed in the body 1.1 distally of the collar 1.2 which is adapted to snap over the barrel 2.1 of the syringe 2. A pair of groove hinges (e.g., recesses) 1.17 may be formed in the body 1.1 adjacent a proximal end of the slot. The c-shaped distal end of the body 1 includes shoulder sections (e.g., projections) 1.4 shaped as a portion of a circle arranged in a transverse plane with respect to a longitudinal axis of the carrier 1. The shoulder sections 14 form circular shoulders adapted to engage the circumferential gap between the barrel 2.1 and the RNS 4.

The syringe 2, with RNS 4 attached to the needle 3, may be loaded into the syringe carrier 1 (e.g., into a recess defined by the syringe carrier 1) by sliding the syringe 2 through the collar 1.2 in the distal direction D. When the RNS 4 abuts the shoulder sections 1.4, the body 1.1 may radially deflect (e.g., rotate) about the groove hinges 1.17. When the RNS 4 bypasses the shoulder sections 1.4, the body 1.1 may return to its non-deflected position and retain the syringe 2 in the syringe carrier 1. The shoulder sections 1.4 engage the circumferential gap between the barrel 2.1 and the RNS 4. Thus, the syringe 2 is prevented from moving axially relative to the syringe carrier 1.

In an exemplary embodiment, the proximal end may include a retainer element which is adapted to provide an abutment surface to prevent the syringe 2 from disengaging the syringe carrier 1 in the proximal direction P.

In an exemplary embodiment, the shoulder sections 1.4 may include proximally-facing contoured surfaces to accommodate a proximal portion of the neck 2.2 of the syringe 2 and distally-facing planar surfaces to abut the RNS 4.

In an exemplary embodiment, a viewing window may be arranged in the body 1.1 for allowing visual access to the barrel 2.1 of the syringe 2 when the syringe 2 is in the syringe carrier 2.

As shown in FIGS. 29 and 30, the finger flange 2.3 includes a first portion that extends radially outward a first distance in a first direction (parallel to the plane of the paper in FIG. 30) and a second portion that extends radially outward a second distance in a second direction (parallel to the plane of the paper in FIG. 29) that is perpendicular to the first direction. The first distance is greater than the second distance.

Still referring to FIGS. 29 and 30, the proximal end of the syringe carrier 1 comprises a first radial protrusion (projection) 1.50 that aligns with and is distally spaced from the first portion of the finger flange 2.3 when the syringe 2 is inserted in the syringe carrier 1, a second radial protrusion (projection) 1.52 opposite the first radial protrusion 1.50, and a circumferential region 1.54 between the first and second radial protrusions 1.50, 1.52 that is free of radial protrusions. The first and second radial protrusions (projections) 1.50, 1.52 extend radially outward from the collar 1.2 and include axial ribs 1.60 and circumferential ribs 1.62.

FIGS. 34-38 show an eighth exemplary embodiment of a syringe carrier 1 according to the present invention. FIG. 34 is a top view of an eighth embodiment of a syringe carrier 1 for supporting a syringe 2. FIG. 35 is a lateral view of the syringe carrier 1 of FIG. 34. FIG. 36 is a longitudinal section of the syringe carrier 1 of FIG. 34 in the section plane A-A. FIG. 37 is a perspective view of the syringe carrier of FIG. 34 without the syringe 2. FIG. 38 is another perspective view of the syringe carrier of FIG. 34.

As shown in FIGS. 34-38, the syringe carrier 1 comprises an elongate body 1.1 arranged to receive the barrel 2.1. In this exemplary embodiment, the body 1.1 has a cylindrical shape with an annular groove 1.19 adjacent its distal end which is adapted to engage a circlip 8. The circlip 8 may engage the circumferential gap between the barrel 1.2 and the RNS 4.

The syringe 2, with RNS 4 attached to the needle 3 and the circlip 8 attached to the syringe 2, may be loaded into the syringe carrier 1 by sliding the syringe 2 into the syringe carrier 1 in the distal direction D. In a non-deflected position, an outer diameter of the circlip 8 may be substantially equal to a diameter of the body 1.1. Thus, when the syringe 2 with the circlip 8 is inserted into the syringe carrier 1, the circlip 8 may deflect radially until the circlip 8 reaches the annular groove 1.19. The circlip 8 may then expand to the non-deflected position and retain the syringe 2 in an axial position relative to the syringe carrier 1. That is, the circlip 8 may engage the annular groove 1.19 and the circumferential gap between the barrel 2.1 and the RNS 4. Thus, the syringe 2 is prevented from moving axially relative to the syringe carrier 1.

In an exemplary embodiment, the proximal end may include a retainer element which is adapted to provide an abutment surface to prevent the syringe 2 from disengaging the syringe carrier 1 in the proximal direction P.

In an exemplary embodiment, the shoulder sections 1.4 may include proximally-facing contoured surfaces to accommodate a proximal portion of the neck 2.2 of the syringe 2 and distally-facing planar surfaces to abut the RNS 4.

In an exemplary embodiment, a viewing window may be arranged in the body 1.1 for allowing visual access to the barrel 2.1 of the syringe 2 when the syringe 2 is in the syringe carrier 2.

FIGS. 39-43 show a ninth exemplary embodiment of a syringe carrier 1 according to the present invention. FIG. 39 is a top view of a ninth embodiment of a syringe carrier 1 for supporting a syringe 2. FIG. 40 is a lateral view of the syringe carrier 1 of FIG. 39. FIG. 41 is a longitudinal section of the syringe carrier 1 of FIG. 39 in the section plane A-A. FIG. 42 is a perspective view of the syringe carrier of FIG. 39 without the syringe 2. FIG. 43 is another perspective view of the syringe carrier of FIG. 39.

As shown in FIGS. 39-43, the syringe carrier 1 comprises an elongate body 1.1 arranged to receive the barrel 2.1. In this exemplary embodiment, the body 1.1 has a cylindrical shape with an annular groove 1.19 having at least one aperture 1.20 adjacent its distal end which is adapted to engage a circlip 8.

The syringe 2, with RNS 4 attached to the needle 3, may be loaded into the syringe carrier 1 by sliding the syringe 2 into the syringe carrier 1 in the distal direction D. When the circumferential gap between the barrel 2.1 and the RNS 4 is aligned with the annular groove 1.19, the circlip 8 may be coupled to the body 1.1 and engage the apertures 1.20. By extending inwardly through the apertures, the circlip 8 may be coupled to the outside of the body 1.1 but engage the circumferential gap between the barrel 2.1 and the RNS 4. The engagement between the circlip 8 and the apertures 1.20 prevents the circlip 8 from translating relative to the body 1.1, and the engagement between the circlip 8 and the circumferential gap prevents the syringe 2 from moving axially relative to the syringe carrier 1.

In an exemplary embodiment, the proximal end may include a retainer element which is adapted to provide an abutment surface to prevent the syringe 2 from disengaging the syringe carrier 1 in the proximal direction P.

In an exemplary embodiment, the shoulder sections 1.4 may include proximally-facing contoured surfaces to accommodate a proximal portion of the neck 2.2 of the syringe 2 and distally-facing planar surfaces to abut the RNS 4.

In an exemplary embodiment, a viewing window may be arranged in the body 1.1 for allowing visual access to the barrel 2.1 of the syringe 2 when the syringe 2 is in the syringe carrier 2.

FIGS. 44-48 show a tenth exemplary embodiment of a syringe carrier 1 and a tool 9 for inserting a syringe 2 into the syringe carrier 1 according to the present invention.

As shown in FIGS. 39-43, the syringe carrier 1 comprises an elongate body 1.1 arranged to receive the barrel 2.1. In this exemplary embodiment, the body 1.1 has an enlarged portion 1.21 on its distal end. The body 1.1 has cylindrical shape with a first diameter and the enlarged portion 1.21 has a second diameter, larger than the first diameter. The enlarged portion 1.21 has one or more resilient barbs 1.22 extending toward a longitudinal axis of the body 1.1 and angled toward a proximal end of the body 1.1.

The syringe 2, with RNS 4 attached to the needle 3, may be loaded into the syringe carrier 1 by inserting the tool 9 into the enlarged portion 1.21 of the syringe carrier 1. The tool 9 may be a cylinder having an open end adapted to receive the RNS 4. The tool 9 may have a third diameter substantially equal to the second diameter. As the tool 9 is inserted into the enlarged portion 1.21, the tool 9 engages and deflects the resilient barbs 1.22. When the barbs 1.22 are deflected, the RNS 4 can pass the barbs 1.22 in the distal direction D and extend from a distal opening of the body 1.1. When a finger flange 2.3 of the syringe 2 abuts a proximal end of the body 1.1, the tool 9 may be removed and the barbs 1.22 may engage the circumferential gap between the barrel 2.1 and the RNS 4 to prevent the syringe 2 from moving axially relative to the syringe carrier 1.

In an exemplary embodiment, the proximal end may include a retainer element which is adapted to provide an abutment surface to prevent the syringe 2 from disengaging the syringe carrier 1 in the proximal direction P.

In an exemplary embodiment, the barbs 1.22 may include proximally-facing contoured surfaces to accommodate a proximal portion of the neck 2.2 of the syringe 2 and distally-facing planar surfaces to abut the RNS 4.

In an exemplary embodiment, a viewing window may be arranged in the body 1.1 for allowing visual access to the barrel 2.1 of the syringe 2 when the syringe 2 is in the syringe carrier 2.

It is apparent to those skilled in the art that the number of deflectable arms 1.3, shoulder sections 1.4, clips 8 may be varied without departing from the spirit and scope of the invention. Likewise, all the illustrated embodiments may be implemented with or without viewing windows 5, projections 1.6, restraining features retainer elements 1.7 and clips. Different kinds of clips may likewise be applied.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A method comprising:
    sliding a syringe into a syringe carrier via a wholly circumferential collar at a proximal end of an elongate body of the syringe carrier, the syringe comprising a barrel, a neck extending distally from the barrel, a finger flange extending from a proximal end portion of the barrel, a needle extending distally from the neck, and a rigid needle shield covering the needle, a portion of the elongate body distal to the collar defining a slot that extends proximally from a distal end of the elongate body such that the distal end of the elongate body is c-shaped, and at least one projection extending radially inward from the distal end of the elongate body, the at least one projection having a proximally-facing contoured surface and a distally-facing planar surface, the proximally-facing contoured surface configured to accommodate the neck of the syringe, the distally-facing planar surface configured to abut a proximal end of the rigid needle shield of the syringe; and
    further sliding the syringe distally such that (i) the rigid needle shield contacts the at least one projection of the distal end of the elongate body and the distal end of the elongate body deflects radially outward, and then (ii) a proximal end of the rigid needle shield moves distal to the at least one projection and the distal end of the elongate body rebounds radially inward such that the at least one projection is disposed in a gap formed between the rigid needle shield and the barrel of the syringe and the at least one projection contacts the barrel of the syringe to restrict distal axial movement of the syringe relative to the syringe carrier,
    wherein the rigid needle shield has an outer diameter greater than an inner diameter defined by the at least one projection when the distal end of the elongate body is in an undeflected position, and the finger flange of the syringe is spaced proximally from the syringe carrier when the at least one projection is in contact with the barrel of the syringe,
    wherein the finger flange of the syringe comprises a first portion that extends radially outward a first distance in a first direction and a second portion that extends radially outward a second distance in a second direction that is perpendicular to the first direction, the first distance being greater than the second distance, and
    wherein the collar at the proximal end of the syringe carrier comprises a first radial protrusion that extends radially outward from the collar and aligns with and is distally spaced from the first portion of the finger flange when the syringe is inserted in the syringe carrier, a second radial protrusion that extends radially outward from the collar and is opposite the first radial protrusion, and a circumferential region between the first and second radial protrusions that is free of radial protrusions, wherein each of the first and second radial protrusions comprises two ribs that extend parallel to one another,
    wherein the elongate body defines a recess adjacent the slot, wherein the recess facilitates radial deflection of the elongate body;
    wherein the elongate body defines a window distal to the collar, and the elongate body comprises a first projection that extends along an edge of the window.

2. The method of claim 1, wherein the elongate body and the at least one projection are integrally formed with one another.

3. The method of claim 1, wherein the slot extends from the distal end of the elongate body approximately to the collar.

4. The method of claim 1, wherein the at least one projection is a single projection.

5. The method of claim 1, wherein the outer diameter of the rigid needle shield is substantially equal to an outer diameter of the barrel of the syringe.

6. The method of claim 1, wherein the outer diameter of the rigid needle shield is greater than the inner diameter defined by the at least one projection when the distal end of the elongate body is rebounded radially inward.

7. The method of claim 1, wherein the syringe contains medicament.

8. The method of claim 1, wherein a distal surface of the distal end of the elongate body is c-shaped.

9. The method of claim 1, wherein the window allows visual access to the barrel of the syringe when the syringe is in the syringe carrier.

10. A method comprising:
sliding a syringe into a syringe carrier via a wholly circumferential collar at a proximal end of an elongate body of the syringe carrier, the syringe comprising a barrel, a neck extending distally from the barrel, a finger flange extending from a proximal end portion of the barrel, a needle extending distally from the neck, and a rigid needle shield covering the needle, a portion of the elongate body distal to the collar defining a slot that extends proximally from a distal end of the elongate body such that the distal end of the elongate body is c-shaped and at least one projection extending radially inward from the distal end of the elongate body, the at least one projection having a proximally-facing contoured surface and a distally-facing planar surface, the proximally-facing contoured surface configured to accommodate the neck of the syringe, the distally-facing planar surface configured to abut a proximal end of the rigid needle shield of the syringe; and
further sliding the syringe distally such that (i) the rigid needle shield contacts the at least one projection of the distal end of the elongate body and the distal end of the elongate body deflects radially outward, and then (ii) a proximal end of the rigid needle shield moves distal to the at least one projection and the distal end of the elongate body rebounds radially inward such that the at least one projection is disposed in a gap formed between the rigid needle shield and the barrel of the syringe and the at least one projection contacts the barrel of the syringe to restrict distal axial movement of the syringe relative to the syringe carrier,
wherein the rigid needle shield has an outer diameter greater than an inner diameter defined by the at least one projection when the distal end of the elongate body is in an undeflected position, and the finger flange of the syringe is spaced proximally from the syringe carrier when the at least one projection is in contact with the barrel of the syringe,
wherein the finger flange of the syringe comprises a first portion that extends radially outward a first distance in a first direction and a second portion that extends radially outward a second distance in a second direction that is perpendicular to the first direction, the first distance being greater than the second distance, and
wherein the collar at the proximal end of the syringe carrier comprises a first radial protrusion that extends radially outward from the collar and aligns with and is distally spaced from the first portion of the finger flange when the syringe is inserted in the syringe carrier, a second radial protrusion that extends radially outward from the collar and is opposite the first radial protrusion, and a circumferential region between the first and second radial protrusions that is free of radial protrusions, wherein each of the first and second radial protrusions comprises a rib extending in a plane perpendicular to a longitudinal axis of the syringe carrier,
wherein the elongate body defines a recess adjacent the slot, wherein the recess facilitates radial deflection of the elongate body; and
wherein the elongate body defines a window distal to the collar, and the elongate body comprises a first projection that extends along an edge of the window.

11. The method of claim 10, wherein the slot extends from the distal end of the elongate body approximately to the collar.

12. The method of claim 10, wherein the at least one projection is a single projection.

13. The method of claim 10, wherein the outer diameter of the rigid needle shield is substantially equal to an outer diameter of the barrel of the syringe.

14. The method of claim 10, wherein a distal surface of the distal end of the elongate body is c-shaped.

15. The method of claim 10, wherein the window allows visual access to the barrel of the syringe when the syringe is in the syringe carrier.

* * * * *